(12) United States Patent
Sakai et al.

(10) Patent No.: US 6,177,474 B1
(45) Date of Patent: Jan. 23, 2001

(54) POLYHYDROXYPHENOL DERIVATIVES AND PREVENTIVE AND THERAPEUTIC AGENTS FOR BONE AND CARTILAGE DISEASES CONTAINING THE SAME

(75) Inventors: Kunikazu Sakai; Yusuke Satoh; Kazuyuki Doi; Kazuyuki Kitamura, all of Saitama-ken (JP)

(73) Assignee: Hoechst Marion Roussel (FR)

( * ) Notice: Under 35 U.S.C. 154(b), the term of this patent shall be extended for 0 days.

(21) Appl. No.: 09/180,756

(22) PCT Filed: May 14, 1997

(86) PCT No.: PCT/JP97/01625

§ 371 Date: Dec. 10, 1998

§ 102(e) Date: Dec. 10, 1998

(87) PCT Pub. No.: WO97/43235

PCT Pub. Date: Nov. 20, 1997

(30) Foreign Application Priority Data

May 14, 1996 (JP) .................................................. 8-154710

(51) Int. Cl.[7] .......................... A61K 31/12; C07C 49/213; C07C 49/713; C07C 49/743
(52) U.S. Cl. ........................ 514/688; 514/690; 568/335; 568/337; 568/377
(58) Field of Search ................................ 568/308, 626, 568/716, 717, 335, 337, 377; 514/727, 685, 678, 729, 690

(56) References Cited

FOREIGN PATENT DOCUMENTS

| | | |
|---|---|---|
| 55-15443 | 2/1980 | (JP) . |
| 55-81814 | 6/1980 | (JP) . |
| 60-155111 | 8/1985 | (JP) . |
| 63-156720 | 6/1988 | (JP) . |
| 63-156722 | 6/1988 | (JP) . |
| 63-156723 | 6/1988 | (JP) . |
| 1242540 | 9/1989 | (JP) . |
| 3218369 | 9/1991 | (JP) . |
| 625081 | 2/1994 | (JP) . |
| 6312924 | 11/1994 | (JP) . |
| 7330594 | 12/1995 | (JP) . |
| 826981 | 1/1996 | (JP) . |
| 827057 | 1/1996 | (JP) . |
| WO9302177 | 2/1993 | (WO) . |

*Primary Examiner*—Sreeni Padmanabhan
(74) *Attorney, Agent, or Firm*—Bierman, Muserlian and Lucas

(57) ABSTRACT

Compounds useful as preventive and therapeutic agents for bone and cartilage diseases; and drug compositions containing the same. The compounds are polyhydroxyphenol derivatives of general formula (I)

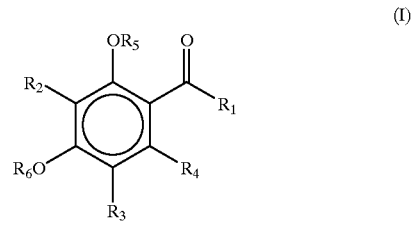

and quinione analogues derived therefrom (wherein $R_1$ is alkyl, optionally substituted benzyl or optionally substituted aryl; $R_2$ is hydrogen, alkyl, alkenyl or optionally substituted benzyl; $R_3$ is hydrogen, alkyl, alkenyl, optionally substituted benzyl, hydroxyl, alkoxy, alkenyloxy or optionally substituted benzyloxy; $R_4$ is hydrogen, alkyl, alkenyl, optionally substituted benzyl or hydroxyl; and $R_5$ and $R_6$ are each independently hydrogen, alkyl, alkenyl or optionally substituted benzyl). The polyhydroxyphenol derivatives and the quinone analogues exhibit a potent inhibitory activity against bone resorption and are useful as preventive and therapeutic agents for bone and cartilage diseases.

17 Claims, No Drawings

POLYHYDROXYPHENOL DERIVATIVES AND PREVENTIVE AND THERAPEUTIC AGENTS FOR BONE AND CARTILAGE DISEASES CONTAINING THE SAME

This is the U.S. National Stage Application of PCT/JP97/01625 filed May 14, 1997.

TECHNICAL FIELD

This invention relates to novel polyhydroxyphenol derivatives, salts thereof, and medicinal compositions containing the same which have been developed for the purpose of being used for preventive and therapeutic osteolytic diseases such as, for example, malignant hypercalcemia, Paget's disease, and osteoporosis and diseases accompanying chondral degeneration and necrosis such as, for example, osteoarthritis apt to attack knees, shoulders, and hip joints, femoral head necrosis, and rheumatoid arthritis.

BACKGROUND ART

Japan has been plunging into such an aging society as has never existed to date and has come to encounter the spread of such osteolytic diseases as osteoporosity as a serious social issue. The term "osteolytic disease" means diseases of bones induced by abnormal aggravation of osteolysis such as, for example, malignant hypercalcemia causes by myeloma and lymphoma, Paget's disease caused by local osteolysis, and osteoporosis caused by various factors like aging and menopause. The growth in the number of aged persons laid up in bed on account of bone fractures which originate in such osteolytic diseases ultimately results in a huge addition to the national medical expenses. At present, vitamin D preparation, calcitonin preparation, and ipriflavone preparation are being used for the therapy of these diseases. The treatment with these medicines allows no radical cure but barely serves as a symptomatic measure. The osteoarthritis, femoral head necrosis, and rheumatoid arthritis form a group of diseases which occur when the articular cartilage and cartilaginified bone are aggravated until degeneration and necrosis by various factors such as, for example, mechanical stress, aging, and inflammation and ultimately suffered to induce defects of bones and cartilages. These chondral defects, by deforming joints and causing pains therein, have a conspicuous effect in the degradation of the quality of daily life of the affected persons. Though the diseases of this category are being treated with hyaluronic acid, anti-inflammatory agent, and analgesic agent, a medicine which is capable of effectively inhibiting or curing chondral defects has not yet been developed.

The object of this invention, therefore, is to improve the existing method of therapy and to provide a novel and more effective preventive and therapeutic medicine.

The present inventors formerly discovered that a substance exhibiting a powerful activity to repress osteolysis is contained in the hops and that the active principle of this substance is an α acid and an iso α acid represented by the following general formula (XIII) (JP-A-07-330594).

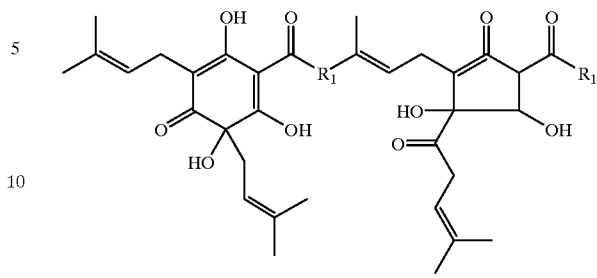

(wherein $R_1$ represents 2-methylpropyl group, 2-propyl group, or 2-butyl group).

It has been pointed out, however, that since the substance (XIII) effective in actively repressing the osteolysis mentioned above is a natural product, it tends to entail such problems as the dependency of the harvest of hops on weather conditions and the difficulty incurred in the procurement thereof. The inventors, with the expectation that the compounds approximating closely to this substance have the possibility of affording active substances as powerful as the aforementioned substance (XIII) capable of repressing osteolysis, have tried structural alterations of the active substance (XIII) mentioned above, synthesized many compounds, and tested them for activity. As a result, they have discovered powerful activity in the polyhydroxyphenol derivatives represented by the general formulas (I)–(XII) to be described herein below. The present invention has been perfected based 0n this discovery.

DISCLOSURE OF THE INVENTION

This invention relates to a compound represented by the following general formula (I)

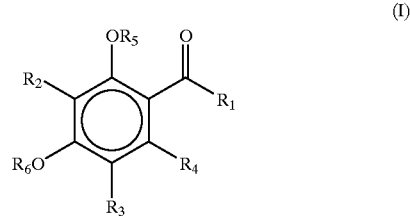

(wherein $R_1$ represents a branched or straight-chain alkyl group of 1–15 carbon atoms, a substituted or unsubstituted benzyl group, or a substituted or unsubstituted aryl group; $R_2$ represents a hydrogen atom, a branched or straight-chain alkyl group of 1–15 carbon atoms, a branched or straight-chain alkenyl group of 2–15 carbon atoms, or a substituted or unsubstituted benzyl group; $R_3$ represents a hydrogen atom, a branched or straight-chain alkyl group of 1–15 carbon atoms, a branched or straight-chain alkenyl group of 2–15 carbon atoms, a substituted or unsubstituted benzyl group, a hydroxyl group, a branched or straight-chain alkoxy group of 1–15 carbon atoms, a branched or straight-chain alkenyloxy group of 2–15 carbon atoms, or a substituted or unsubstituted benzyloxy group; $R_4$ represents a hydrogen atom, a branched or straight-chain alkyl group of 1–15 carbon atoms, a branched or straight-chain alkenyl group of 2–15 carbon atoms, a substituted or unsubstituted benzyl group, or a hydroxyl group; and $R_5$ and $R_6$ independently represent a hydrogen atom, a branched or straight-chain alkyl group of 1–15 carbon atoms, a branched or straight-chain alkenyl group of 2–15 carbon atoms, or a substituted or unsubstituted benzyl group; providing that the case in which $R_2$ and $R_3$ are each a hydrogen atom or a 3-methyl-2-butenyl group when $R_4$ is a hydroxyl group, $R_5$ and $R_6$ are each a hydrogen atom, and $R_1$ is a 2-propyl group or 2-butyl group and the case in which $R_2$ and $R_3$ are each a hydrogen atom, a 3-methyl-2-butenyl group, or a 3-methyl-n-butyl group when $R_4$ is a hydroxyl group, $R_5$ and $R_6$ are each a hydrogen atom, and $R_1$ is a 2-methylpropyl group are excluded) or an acylfluoroglucinol derivative thereof which is a salt thereof.

More specifically, this invention relates to a compound represented by the following general formula (II)

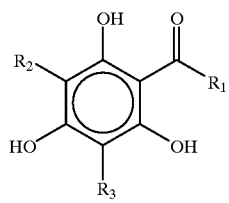

(II)

(wherein $R_1$ represents a 2-methylpropyl group or a 2,6-dimethylheptyl group; and $R_2$ and $R_3$ independently represent a hydrogen atom, a 3-methyl-2-butenyl group, a 3,7-dimethyl-2,6-octadienyl group, or a substituted or unsubstituted benzyl group; providing that the case in which $R_1$ is a 2-methylpropyl group and $R_2$ and $R_3$ independently are a hydrogen atom or a 3-methyl-2-butenyl group is excluded)

or an acylfluoroglucinol derivative thereof which is a salt thereof and a compound represented by the following general formula (III)

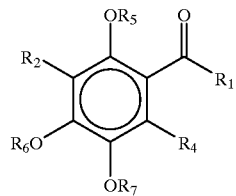

(III)

(wherein $R_1$ represents a branched or straight-chain alkyl group of 1–15 carbon atoms, a substituted or unsubstituted benzyl group, or a substituted or unsubstituted aryl group; $R_2$ and $R_4$ independently represent a hydrogen atom, a branched or straight-chain alkyl group or alkenyl group of 1–15 carbon atoms, or a substituted or unsubstituted benzyl group; and $R_5$, $R_6$, and $R_7$ independently represent a hydrogen atom, a branched or straight-chain alkyl group or alkenyl group of 1–15 carbon atoms, or a substituted or unsubstituted benzyl group) or an acylhydroxyhydroquinone derivative thereof which is a salt thereof.

This invention further relates to a compound represented by the following general formula (IV)

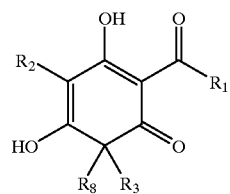

(IV)

(wherein $R_1$ represents a branched or straight-chain alkyl group of 1–15 carbon atoms, a substituted or unsubstituted benzyl group, or a substituted or unsubstituted aryl group; $R_2$ represents a hydrogen atom, a branched or straight-chain alkyl group of 1–15 carbon atoms, a branched or straight-chain alkenyl group of 2–15 carbon atoms, or a substituted or unsubstituted benzyl group; $R_3$ represents a branched or straight-chain alkyl group of 1–15 carbon atoms, a branched or straight-chain alkenyl group of 2–15 carbon atoms, or a substituted or unsubstituted benzyl group; and $R_8$ represents a hydroxyl group, a branched or straight-chain alkyl group of 1–15 carbon atoms, a branched or straight-chain alkenyl group of 2–15 carbon atoms, or a substituted or unsubstituted benzyl group; providing that the case in which $R_2$ and $R_3$ are each a 3-methyl-2-butenyl group when $R_1$ is a methyl group and $R_8$ is a hydroxyl group and the case in which at least two or three members of the class consisting of $R_2$, $R_3$, and $R_8$ are each a 3-methyl-2-butenyl group and the remaining member is a hydrogen atom or a hydroxyl group when $R_1$ is a 2-propyl group or 2-methylpropyl group are excluded) or an acyldihydroxycyclohexadienone derivative thereof which is a salt thereof.

More specifically, this invention relates to a compound represented by the following general formula (V)

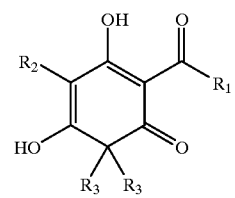

(V)

(wherein $R_1$ represents a 2-methylpropyl group or a 2,6-dimethylheptyl group; $R_2$ represents a hydrogen atom, a 3-methyl-2-butenyl group, a 3,7-dimethyl-2,6-octadienyl group, or a substituted or unsubstituted benzyl group; and $R_3$ represents a 3-methyl-2-butenyl group, a 3,7-dimethyl-2,6-octadienyl group, or a substituted or unsubstituted benzyl group; providing that the case in which $R_1$ is a 2-methylpropyl group or a 2-propyl group, $R_2$ is a hydrogen atom or a 3-methyl-2-butenyl group, and $R_3$ is a 3-methyl-2-butenyl group is excluded) or an acyldihydroxycyclohexadienone derivative thereof which is a salt thereof and a compound represented by the following general formula (VI)

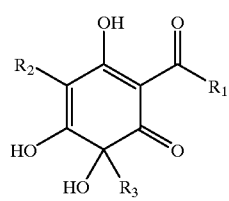

(VI)

(wherein $R_1$ represents a 2-methylpropyl group or a substituted or unsubstituted aryl group; and $R_2$ and $R_3$ each represent a 3-methyl-2-butenyl group, or a substituted or unsubstituted benzyl group; providing that the case in which $R_1$ is a 2-methylpropyl group and $R_2$ and $R_3$ are each a 3-methyl-2-butenyl group is excluded) or an acyltrihydroxycyclohexadienone derivative thereof which is a salt thereof.

Further, this invention relates to a medicinal composition composed of a compound represented by the general formula (VII).

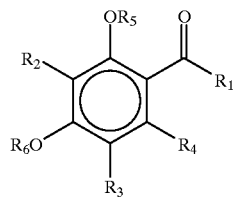

(VII)

(wherein $R_1$ represents a branched or straight-chain alkyl group of 1–15 carbon atoms, a substituted or unsubstituted benzyl group, or a substituted or unsubstituted aryl group; $R_2$ represents a hydrogen atom, a branched or straight-chain alkyl group of 1–15 carbon atoms, a branched or straight-chain alkenyl group of 2–15 carbon atoms, or a substituted or unsubstituted benzyl group; $R_3$ represents a hydrogen atom, a branched or straight-chain alkyl group of 1–15 carbon atoms, a branched or straight-chain alkenyl group of 2–15 carbon atoms, a substituted or unsubstituted benzyl group, a hydroxyl group, a branched or straight-chain alkoxy group of 1–15 carbon atoms, a branched or straight-chain alkenyloxy group of 2–15 carbon atoms, or a substituted or unsubstituted benzyloxy group; $R_4$ represents a hydrogen atom, a branched or straight-chain alkyl group of 1–15 carbon atoms, a branched or straight-chain alkenyl group of 2–15 carbon atoms, a branched or straight-chain benzyl group, or a hydroxyl group; and $R_5$ and $R_6$ each independently represent a hydrogen atom, a branched or straight-chain alkyl group of 1–15 carbon atoms, a branched or straight-chain alkenyl group of 2–15 carbon atoms, or a substituted or unsubstituted benzyl group) or one or more pharmaceutically acceptable salts thereof and a pharmaceutically acceptable carrier therewith.

Specifically, this invention relates to a medicinal composition containing an acylfluoroglucinol derivative which is a compound represented by the following general formula (VIII)

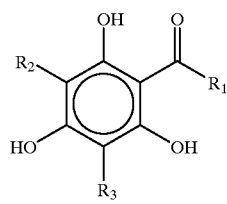

(VIII)

(wherein $R_1$ represents a 2-methylpropyl group or a 2,6-dimethylheptyl group; and $R_2$ and $R_3$ each independently represent a hydrogen atom, a 3-methyl-2-butenyl group, a 3,7-dimethyl-2,6-octadienyl group, or a substituted or unsubstituted benzyl group) or a pharmaceutically acceptable salt thereof and an acylhydroxyhydroquinone derivative which is a compound represented by the following general formula (IX)

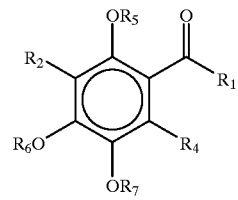

(IX)

(wherein $R_1$ represents a branched or straight-chain alkyl group of 1–15 carbon atoms, a substituted or unsubstituted benzyl group, or a substituted or unsubstituted aryl group; $R_2$ and $R_4$ each independently represent a hydrogen atom, a branched or straight-chain alkyl group or alkenyl group of 1–15 carbon atoms, or a substituted or unsubstituted benzyl group; and $R_5$, $R_6$, and $R_7$ each independently represent a hydrogen atom, a branched or straight-chain alkyl group or alkenyl group of 1–15 carbon atoms, or a substituted or unsubstituted benzyl group) or one or more pharmaceutically acceptable salts thereof and a pharmaceutically acceptable carrier therewith.

This invention further relates to a medicinal composition containing an acyldihydroxycyclohexadienone derivative which is a compound represented by the following general formula (X)

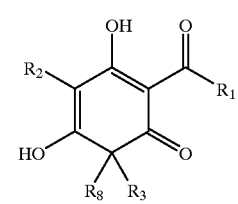

(X)

(wherein $R_1$ represents a branched or straight-chain alkyl group of 1–15 carbon atoms, a substituted or unsubstituted benzyl group, or a substituted or unsubstituted aryl group; $R_2$ represents a hydrogen atom, a branched or straight-chain alkyl group of 1–15 carbon atoms, a branched or straight-chain alkenyl group of 2–15 carbon atoms, or a substituted or unsubstituted benzyl group; $R_3$ represents a branched or straight-chain alkyl group of 1–15 carbon atoms, a branched or straight-chain alkenyl group of 2–15 carbon atoms, or a substituted or unsubstituted benzyl group; and $R_8$ represents a hydroxyl group, a branched or straight-chain alkyl group of 1–15 carbon atoms, a branched or straight-chain alkenyl group of 2–15 carbon atoms, or a substituted or unsubstituted benzyl group) or one or more pharmaceutically acceptable salts thereof and a pharmaceutically acceptable carrier therewith.

More specifically, this invention relates to a medicinal composition containing an acyldihydroxycyclohexadienone derivative which is a compound represented by the following general formula (XI)

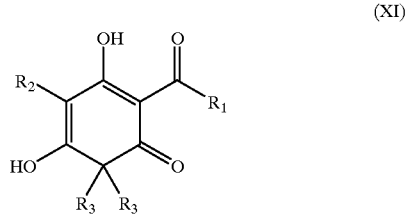

(XI)

(wherein $R_1$ represents a 2-methylpropyl group or a 2,6-dimethylheptyl group; $R_2$ represents a 3-methyl-2-butenyl group, a 3,7-dimethyl-2,6-octadienyl group, or a substituted or unsubstituted benzyl group; and $R_3$ represents a 3-methyl-2-butenyl group, a 3,7-dimethyl-2,6-octadienyl group, or a substituted or unsubstituted benzyl group) or a pharmaceutically acceptable salt thereof and an acyltrihydroxycyclohexadienone derivative which is a compound represented by the following general formula (XII)

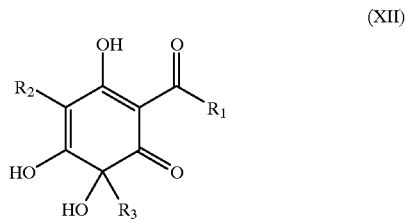

(XII)

(wherein $R_1$ represents a 2-methylpropyl group or a substituted or unsubstituted aryl group; and $R_2$ and $R_3$ each represent a 3-methyl-2-butenyl group, or a substituted or unsubstituted benzyl group) or one or more pharmaceutically acceptable salts thereof and a pharmaceutically acceptable carrier therewith.

Further, this invention relates to a preventive and therapeutic method for a disease affecting bone and cartilage, which method comprises administering to the patient of the disease one or more members selected from the group consisting of the compounds represented by the general formulas (I), (IV), (IIV), and (X) in an amount effective in preventing or curing the disease. It further relates to the use of one or more members selected from the group consisting of the compounds represented by the general formulas (I), (IV), (IIV), and (X) for the production of a medicinal composition intended for the prevention or therapy of a disease affecting bone and cartilage.

The medicinal composition of the present invention possesses an activity to inhibit osteolysis and, therefore, is useful as a preventive and therapeutic agent for the diseases affecting bone and cartilage.

MODE OF EMBODIMENT OF THE INVENTION

The alkyl group in the compound of this invention is a branched or straight-chain alkyl group of 1–15 carbon atoms, preferably 1–10 carbon atoms. A methyl group, an n-propyl group, an isopropyl group, an n-butyl group, a sec-butyl group, an isobutyl group, varying pentyl groups, varying hexyl groups, and varying heptyl groups may be cited as concrete examples of the alkyl group. As the alkyl groups denoted by the substituent, $R_1$, 2-propyl group, 2-methylpropyl group, 2,6-dimethylheptyl group, and 2,6,10-trimethylundecanyl group are preferred concrete examples.

The alkenyl group in the compound is a branched or straight-chain alkenyl group of 2–15 carbon atoms, preferably 2–10 carbon atoms, possessing one or more unsaturated carbon-carbon bonds. A vinyl group, an allyl group, a butenyl group, a pentenyl group, and an octadienyl group may be cited as concrete examples of the alkenyl group. Preferably, 3-methyl-2-butenyl group, 3,7-dimethyl-2,6-octadienyl group, and 3,7,11-trimethyl-2,6,10-dodecatrienyl group may be cited as other examples.

As concrete examples of the aryl group in the compound, heterocyclic aromatic substituents such as a pyridine ring, a pyrimidine ring, a pyrrole ring, an imidazole ring, and a thiophene ring may be cited besides the groups possessing a six-member aromatic ring. Preferably, a phenyl group, a naphthyl group, etc. may be cited. Particularly preferably, a phenyl group may be cited.

The aryl group and the benzyl group may be substituted with a varying substituent so long as the substitution may not impair the physiological activity of the compound of this invention. As concrete examples of the substituent, halogen atoms such as chlorine, fluorine, and bromine, a hydroxyl group, alkoxy groups of 1–15 carbon atoms, alkenyloxy groups of 2–15 carbon atoms, and acyl groups such as acetyl group and propionyl group may be cited.

As preferred concrete examples of the compound represented by the general formula (I) according to this invention, (2,4,6-Trihydroxyphenyl) (2,6-dimethylheptyl) ketone (Compound No. 6), {3-(3-Methyl-2-butenyl)-2,4,6-trihydroxyphenyl} (2,6-dimethylheptyl) ketone (Compound No. 23), {3,5-Bisbenzyl-2,4,6-trihydroxyphenyl} (2-methylpropyl) ketone (Compound No. 34), {3,5-Bis(3,7-dimethyl-2,6-octadienyl)-2,4,6-trihydroxyphenyl)} (2-methylpropyl) ketone (Compound No. 19), {(3-(3-Methyl-2-butenyl)-2,4,5-trihydroxyphenyl} (2-methylpropyl) ketone (Compound No. 26), {3,6-Bis(3-methyl-2-butenyl)-2,4,5-trihydroxyphenyl} (2-methylpropyl) ketone (Compound No. 25), {(6-(3-Methyl-2-butenyl)-2,4,5-trihydroxyphenyl} (2-methylpropyl) ketonemono(3-methyl-2-butenyl) ether (Compound No. 27), (2,4,5-Trihydroxyphenyl) (2-methylpropyl) ketonemono (3-methyl-2-butenyl) ether (Compound No. 28), {3,5-Bis(3-methyl-2-butenyl)-2,4,6-trihydroxyphenyl)} (phenylmethyl) ketone (Compound No. 39), {3-(3-Methyl-2-butenyl)-2,4,6-trihydroxyphenyl)} (phenylmethyl) ketone (Compound No. 42), {3,5-Bis(3,7-dimethyl-2,6-octadienyl)-2,4,6-trihydroxyphenyl)} (phenylmethyl) ketone (Compound No. 43), {3-(3,7-Dimethyl-2,6-octadienyl)-2,4,6-trihydroxyphenyl)} (phenylmethyl) ketone (Compound No. 46), {2-Hydroxy-6-methyl-4-(3-methyl-2-butenyloxy) phenyl} (2-methylpropyl) ketone (Compound No. 48), {2,4-Dihydroxy-6-methyl-3-(3-methyl-2-butenyl) phenyl} (2-methylpropyl) ketone (Compound No. 49), {4,6-Dihydroxy-2-methyl-3-(3-methyl-2-butenyl) phenyl} (3-methylpropyl) ketone (Compound No. 50), {3,5-Bis(3-methyl-2-butenyl)-2-hydroxy-6-methyl-4-(3-methyl-2-butenyloxy)phenyl)} (2-methylpropyl) ketone (Compound No. 51), {2-Hydroxy-4-(3-methyl-2-butenyloxy)phenyl} (2-methylpropyl) ketone (Compound No. 53), {2,4-Dihydroxy-3-(3-methyl-2-butenyl)phenyl} (2-methylpropyl) ketone (Compound No. 54), and {2,4-Dihydroxy-5-(3-methyl-2-butenyl)phenyl} (2-methylpropyl) ketone (Compound No. 55) may be cited.

As concrete examples of the compound represented by the general formula (IV) of this invention, 2,2-bis(3,7-dimethyl-2,6-octadienyl)-3,5-dihydroxy-6-(3-methyl-1-oxobutyl)cyclohexa-3,5-dienone (Compound No. 21), 3,5-dihydroxy-6-(3-methyl-1-oxobutyl)-2,2,4-tris(3,7-dimethyl-2,6-octadienyl)cyclohexa-3,5-dienone (Compound No. 20), 2,2-bisbenzyl-3,5-dihydroxy-6-(3-methyl-1-oxobutyl)-cyclohexa-3,5-dienone (Compound No. 35), 3,5-dihydroxy-6-(3-methyl-1-oxobutyl)-2,2,4-trisbenzylcyclohexa-3,5-dienone (Compound No. 36), 2,2-bis(3-methyl-2-butenyl)-3,5-dihydroxy-6-(3,7-dimethyl-1-oxooctyl)cyclohexa-3,5-dienone (Compound No. 24), 3,5-dihydroxy-6-(3,7-dimethyl-1-oxooctyl)-2,2,4-tris(3-methyl-2-butenyl)cyclohexa-3,5-dienone (Compound No. 22), 2,4-bis(3-methyl-2-butenyl)-6-(benzoyl)-2,3,5-trihydroxycyclohexa-3,5-dienone (Compound No. 32), 2,4-dimethyl-6-(3-methyl-1-oxobutyl)-2,3,5-trihydroxycyclohexa-3,5-dienone (Compound No. 31), 2,4-bisbenzyl-6-(3-methyl-1-oxobutyl)-2,3,5-trihydroxycyclohexa-3,5-dienone (Compound No. 33), 3,5-dihydroxy-6-(phenylacetyl)-2,2,4-tris(3-methyl-2-butenyl)cyclohexa-3,5-dienone (Compound No. 40), 3,5-dihydroxy-6-(phenylacetyl)-2,2-bis(3-methyl-2-butenyl)cyclohexa-3,5-dienone (Compound 41), 3,5-dihydroxy-6-(phenylacetyl)-2,2,4-tris(3,7-dimethyl-2,6-octadienyl)cyclohexa-3,5-dienone (Compound No. 44), and 3,5-dihydroxy-6-(phenylacetyl)-2,2-bis(3,7-dimethyl-2,6-octadienyl)cyclohexa-3,5-dienone (Compound No. 45) may be cited.

The compound of this invention may form a salt with such an inorganic base as the hydroxide of an alkali metal or such an organic base as organic amine, may form a solvation product with such a solvent as water.

In the compounds represented by the general formula (I), those having 2-propyl group, 2-methylpropyl group, or 2-butyl group for $R_1$ and 3-methyl-2-butenyl group for each of $R_2$ and $R_3$ are the substances which are known to be contained in the hops as the precursor of the α acid indicated as the substance (XIII) having the aforementioned activity to repress osteolysis (R. Stevens, Chemical Reviews, 1967, 19 refers).

In the compounds represented by the general formula (I) or (IV), those having 2-propyl group, 2-methylpropyl group, or 2-butyl group for $R_1$ and 3-methyl-2-butenyl group or 3-methylbutyl group for each of $R_2$ and $R_3$ have been found by assay to possess an antimicroorganic activity as a hop-related compound (S. Mizobuchi and Y. Sato, Agric. Biol. Chem., 49, 399 (1985) refers).

The fact that the series of compounds represented by any one of the general formulas (I)–(XII) as proposed by the present invention exhibit a powerful activity to repress osteolysis, however, has never been known to the art and it has been discovered for the first time by the present inventors.

This invention, therefore, relates to medicinal compositions which contain compounds represented by any one of the general formulas (VII)–(XII) mentioned above or one or more pharmaceutically acceptable salts thereof as an active principle. The medicinal compositions of this invention are allowed to contain a varying pharmaceutically acceptable carrier.

The medicinal compositions of this invention possess an activity to inhibit osteolysis and, therefore, are useful as a preventive and therapeutic agent for diseases affecting bone and cartilage.

The term "bone and cartilage disease" as used in this invention means osteolytic diseases such as, for example, malignant hypercalcemia, Paget's disease, and osteoporosis and diseases accompanying chondral degeneration and necrosis such as, for example, osteoarthritis apt to attack knees, shoulders, and hip joints, femoral head necrosis, and rheumatoid arthritis.

The polyhydroxyphenol derivatives represented by the general formulas (I)–(VI) of the present invention and the medicinal compositions represented by the general formulas (VII)–(XII) of the present invention can be produced by the process of the reactions shown in Table 1 below.

The method for production shown in Table 1 will be described specifically.

First Step

This step consists in effecting acylation of a polyhydroxybenzene under the Friedel-Crafts reaction conditions. The polyhydroxybenzenes (a) and (b) are easily available commercially and the polyhydroxybenzene (c) can be manufactured from picric acid by the method proposed by Ohara et al. (Junichi Onodera and Heitaro Ohara, Journal of the Chemical Society of Japan, 1973, 1808 refers). As concrete examples of the acylating agent (RCOX) to be used in this step, acetyl chloride, acetyl bromide, acetic anhydride, butyryl chloride, butyryl bromide, butyric anhydride, isobutyryl chloride, isobutyryl bromide, isobutyric anhydride, 2-butyryl chloride, 2-butyryl bromide, 2-butyric anhydride, isovaleryl chloride, isovaleryl bromide, isovaleric anhydride, 3,7-dimethyl octanoyl chloride, 3,7-dimethyl octanoyl bromide, 3,7-dimethyl octanoic anhydride, phenylacetyl chloride, phenylacetyl bromide, phenylacetic anhydride, benzoyl chloride, benzoyl bromide, and benzoic anhydride may be cited. As concrete examples of the acid catalyst to be used in the reaction, the reagents which are generally used in the Friedel-Crafts reaction such as aluminum bromide, aluminum chloride, antimony chloride, iron chloride, titanium chloride, tin chloride, bismuth chloride, zinc chloride, boron fluoride, hydrogen fluoride, sulfuric acid, and polyphosphoric acid may be cited. Among other reagents cited above, aluminum chloride is used particularly advantageously. The acid catalyst is used in an amount in the approximate range of 1–3 mols. The reaction is carried out in a solvent. As concrete examples of the solvent used for the reaction, nitromethane, nitrobenzene, carbon disulfide, dichloromethane, carbon tetrachloride, and 1,2-dichloroethane may be cited. From the viewpoint of solubility, for example, nitrobenzene or a mixture of nitrobenzene with carbon disulfide is advantageously used.

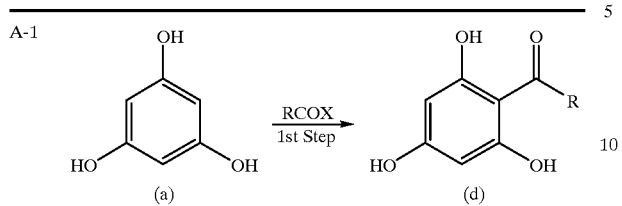

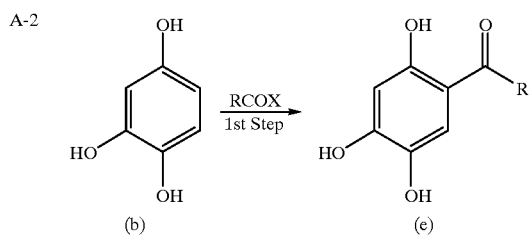

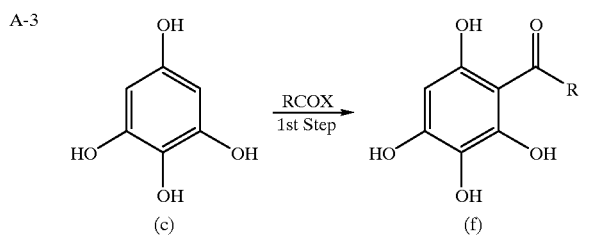

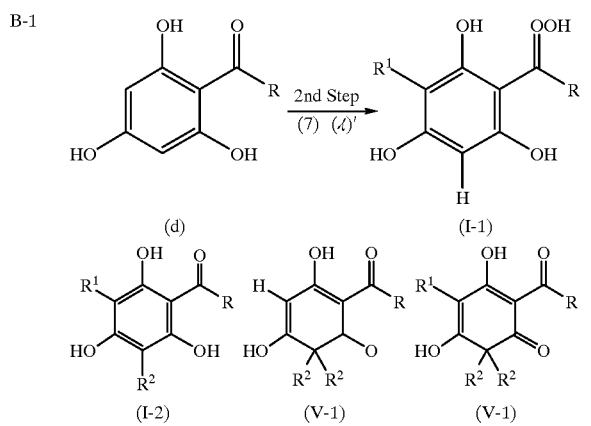

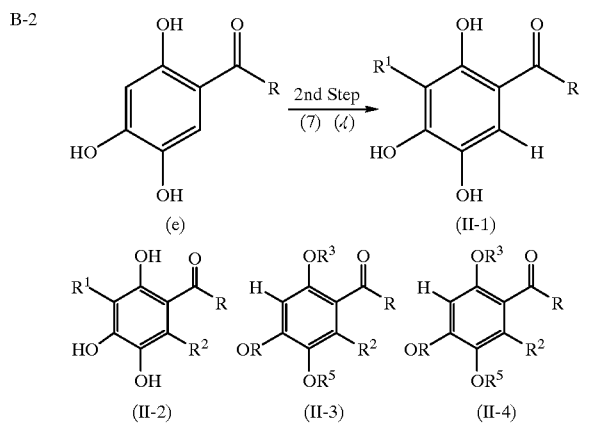

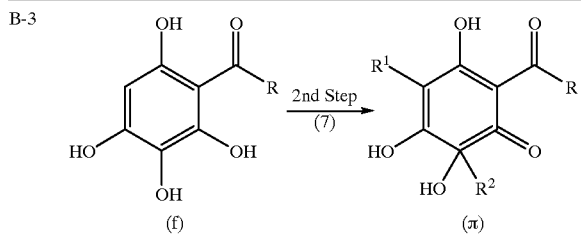

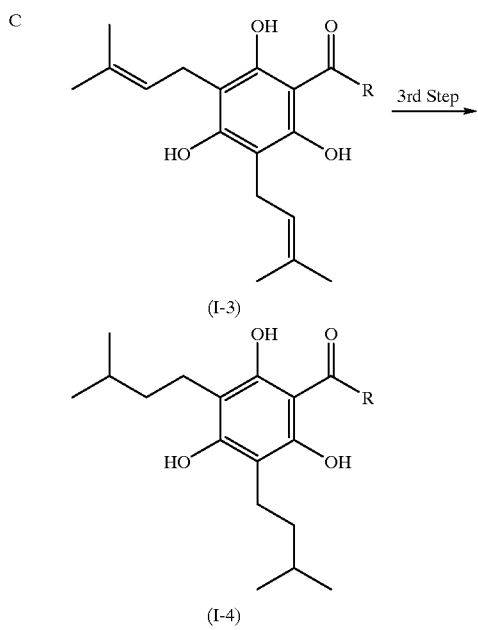

Though the reaction temperature is in the range of 0° C.–150° C., the reaction proceeds thoroughly at room temperature. The compounds (d), (e), and (f) which are produced by the step described above are used in the next step.

Second Step

This step consists in introducing an alkyl group or an alkenyl group into the acylated polyhydroxybenzene (d), (e), or (f). The reaction of this step can be effectively carried out under the basic or the acidic conditions.

(i) Reaction Under Basic Conditions

Under this condition, the acylated polyhydroxybenzene (d), (e), or (f) is converted into a corresponding salt by the reaction of a base and the resultant salt is reacted on by an alkylating agent or alkenylating agent. As concrete examples of the base to be used herein, alkali metal hydroxides such as sodium hydroxide and potassium hydroxide, alkali metal alkoxides such as sodium methoxide, potassium methoxide, sodium ethoxide, potassium ethoxide, sodium t-butoxide, and potassium t-butoxide, alkali metal hydrides such as sodium hydride, potassium hydride, and lithium hydride, alkyl lithium compounds such as methyl lithium, n-butyl lithium, and phenyl lithium, and aryl lithium compounds may be cited. The reaction is carried out in a solvent. As concrete examples of the solvent, water, alcohols such as methanol, ethanol, and t-butanol, ethers such as ethyl ether, isopropyl ether, tetrahydrofuran, and 1,4-dioxane, dimethylsulfoxide, N,N-dimethylformamide and N-methylpyrrolidone, and aromatic compounds such as benzene and toluene may be cited. The solvent is properly selected to suit the character of the base to be used. As concrete examples of the alkylating agent mentioned above, methyl iodide, bromoethane, 1- or 2-bromopropane, 1- or 2-chloropropane, 1- or 2-bromobutane, 2-methyl-1-bromopropane, 1-bromopentane, 2-chloropentane, 3-methyl-1-bromobutane, 1-bromooctane, 1-chlorooctane, benzyl bromide, benzyl chloride, and bromomethyl thiophene may be cited. As concrete examples of the alkenylating agent mentioned above, allyl bromide, allyl chloride, 1-bromo-2-butene, 1-chloro- 2-butene, 3-methyl-1-bromo-2-butene, 3-methyl-1-chloro-2-butene, 3,7-dimethyl-1-bromo-2,6-octadiene, and 3,7-dimethyl-1-chloro-2,6-octadiene may be cited.

(ii) Reaction Under Acidic Conditions

Though this reaction can be carried out under the standard Friedel-Crafts conditions which are used in the first step mentioned above, it is advantageously carried out in ethyl ether, 1,4-dioxane, or methylene chloride by using boron fluorideether (BF3-Et2) (E. Collins and P. V. R. Shannon, J. Chem. Soc., Perkin Trans., 1, 1973, 419. refers). As concrete examples of the alkylating agent to be used herein, saturated alcohols such as methanol, ethanol, butanol, 3-methyl butanol, pentanol, and decanol, and allyl alcohols such as allyl alcohol, 2-butenol, 3-methyl-2-butenol, and 3,7-dimethyl-2,6-octadienol may be cited.

By this step, an acyl fluoroglucinol derivative and an acyl dihydroxycyclohexadienone derivative of this invention are obtained from the compound (d), an acyl hydroxyhydroquinone derivative of this invention is obtained from the compound (e), and an acyl dihydroxycyclohexadienone derivative of this invention is obtained from the compound (f).

Third Step

This step consists in reducing the double bond of the allyl derivative (I-3) produced at the second step and consequently producing an alkyl derivative (I-4). Though the standard method for reducing a double bond is utilized at the present step, the method resorting to catalytic hydrogenation is used advantageously. The catalysts usable for the catalytic hydrogenation include platinum oxide, palladium-carbon, and rhodium-carbon, for example. As concrete examples of the solvent which is used advantageously herein, alcohols such as methanol and ethanol and esters such as ethyl acetate and butyl acetate may be cited. Though the reaction temperature is in the range of 0° C.–100° C., the reaction is advantageously performed at room temperature.

The polyhydroxyphenol derivative produced as described above was tested for activity to inhibit osteolysis by the pit formation assay method. It was consequently found to exhibit inhibition of osteolysis at an outstanding ratio in a concentration of $1 \times 10^{-5}$ M (Refer Example 26 and Tables 2 and 3 which will be described herein below.).

Though the clinical dosage of the compound of this invention depends on such factors as the method of administration, the status of disease, and the condition of a patient, it is generally in the range of 0.1 g–2 g per adult per day (about 1.5 mg–30 mg/Kg/day). The administration of this compound is attainable intravenously, intramuscularly, orally, and per rectum. The intravenous administration may be effected by drip phleboclysis besides the standard intravenous injection. The medicine containing the compound of this invention is produced by the standard method using standard excipient and additives.

The medicine for injection can be produced, for example, in the form of a powdery preparation fit for injection. In this case, the preparation can be obtained by solving the compound in water incorporating therein one or more suitable water-soluble excipients selected from among mannitol, sucrose, lactose, maltose, glucose, and fructose, dispensing the resultant solution in vials or ampoules, freeze drying the solution in the containers, and hermetically sealing the containers. The medicine for oral administration can be obtained in the standard forms of tablets, capsules, granules, fine particles, and powder and in an intestinally soluble preparation as well.

The intestinally soluble preparation can be obtained by molding the compound into tablets, granules, fine particles, etc., when necessary in combination with additives including a lubricant such as, for example, mannitol, sucrose, lactose, maltose, starch, silicic anhydride, or calcium phosphate, a binding agent such as, for example, carboxymethyl cellulose, methyl cellulose, gelatin, or gum arabic, and a disintegrator such as, for example, carboxymethyl cellulose calcium, and then coating the molded particles with one or more intestinally soluble bases selected from among cellulose acetophthalate, hydroxypropyl methyl cellulose phthalate, hydroxypropyl methyl cellulose acetyl succinate, polyvinyl alcohol phthalate, styrene, maleic anhydride copolymer, styrene-maleic acid copolymer, methyl methacrylate-methacrylic acid copolymer, and methyl acrylate-methacrylic acid copolymer, when necessary in combination with a coloring agent such as, for example, titanium oxide. The intestinally soluble granules or fine particles may be packed in capsules and used as capsuled medicines. Otherwise, the capsuled medicines produced by the standard method may be vested with intestinal solubility by being coated with the intestinally soluble base mentioned above. Alternatively, an intestinally soluble capsuled medicine may be obtained by using capsules which are made solely of the intestinally soluble base exclusively or in combination with gelatin.

The suppository can be obtained by homogeneously blending the compound with an oleophilic base such as, for example, a semisynthetic base prepared by mixing cacao butter or fatty acid triglyceride with fatty acid monoglyceride or fatty acid diglyceride at a varying ratio and a hydrophilic base such as, for example, polyethylene glycol or glycerogelatin and molding the resultant blend in a die.

The polyhydroxyphenol derivative which is provided by this invention possesses a powerful activity to inhibit osteolysis and, therefore, can be utilized as a preventive and therapeutic agent for diseases affecting bone and cartilage.

EXAMPLES

Now, this invention will be described more specifically below with the aid of referential examples, examples, and test examples, which are meant to be illustrative of and not limited in any respect of the present invention.

Referential Example 1

Synthesis of (2-propyl)(2,4,6-trihydroxyphenyl) ketone (4)

In a vessel fitted with a calcium chloride tube, 12.61 g (100.0 mmol) of 1,3,5-trihydroxybenzene (1) was suspended on a mixture of 35 ml of nitrobenzene and 45 ml of carbon disulfide and they were stirred. To the mixture, 40.0 g (300 mmol, 3.00 equivalents) of granular aluminum chloride was added piecemeal at room temperature. They were stirred for one hour and a nitrobenzene (10.0 ml) solution of 10.66 g (100.0 mmol, 1.000 equivalent) of isobutyryl chloride was slowly added dropwise to the mixture. After about 5 hours, the reaction mixture was poured into a cold 2 M hydrochloric acid (500 ml) solution to induce decomposition of aluminum salt and then was extracted from ether. The organic layer was washed with water and distilled off ether under a reduced pressure. To this was added a large amount of water and water was distilled under reduced pressure to remove nitrobenzene solvent by steam distillation method. The residue was dissolved in ether, washed with saturated brine, dried over sodium sulfate, and distilled under a reduced pressure to remove the solvent and obtain 21.7 g of a crude reaction product. By recrystallization of the crude product from petroleum ether-methylene chloride (1:1), 17.1 g (yield 87.2%) of the product (4) was obtained in the form of light yellow powdery crystals.

1HNMR δ (TMS): 1.10 (6H, d, J=7.0 Hz), 3.92 (1H, sept, J=7.0 Hz), 5.83 (2H, s), 9.93 (1H, bs), 12.1 (2H, bs).

Referential Example 2
Synthesis of (2-methylpropyl) (2,4,6-trihydroxyphenyl) ketone (5)

A crude reaction product was obtained by repeating the procedure of Referential Example 1 while using 12.06 g (100.0 mmol) of isovaleryl chloride instead. The crude product was recrystallized from petroleum ether to obtain 16.7 g (yield 76.9%) of the compound (5) in the form of lightly colored fine powder crystals.

1HNMR δ (TMS): 0.95 (6H, d, J=6.6 Hz), 2.21 (1H, sept, J=6.6), 2.90 (2H, d, J=6.6 Hz), 5.86 (2H, s), 9.86 (1H, s), 12.01 (2H, s).

Example 1
Synthesis of (2,6-dimethylheptyl) (2,4,6-trihydroxyphenyl) ketone (6)

Under the atmosphere of nitrogen, a solvent mixture of 27 ml of nitrobenzene and 23 ml of carbon disulfide was added to 6.613 g (52.4 mmol) of 1,3,5-trihydroxybenzene (1). To the mixture, 21 g (157.2 mmol, 3 equivalents) of granular aluminum chloride was added cooling with ice and stirred for two hours. Into the mixture thus formed, was added a nitrobenzene (8 ml) solution of 10.87 g (57.0 mmol, 1.09 equivalents) of 3,7-dimethyl-octanoyl chloride dropwise and were stirred at room temperature for 21 hours. The reaction mixture was poured into a cold dilute hydrochloric acid solution prepared by adding 5 ml of concentrated hydrochloric acid to 200 ml of ice and stirred and extracted from ether. The organic layer was washed with saturated brine, dried over sodium sulfate, and distilled under a reduced pressure to remove the solvent. To the residue of distillation, a large volume of water was added and were distilled under reduced pressure to remove nitrobenzene solvent by steam distillation method. The residue was extracted from ether, washed with saturated brine, dried over sodium sulfate, and distilled under a reduced pressure to remove the solvent and obtain a crude reaction product. By subjecting the crude product to silica gel column chromatography (using 100 g of Wako Gel C-200, elution with hexane:ethyl acetate=7:3), 9.25 g of (2,4,6-trihydroxyphenyl) (2,6-dimethylheptyl) ketone (6) was obtained in the form of an oily substance.

1HNMR δ (TMS): 0.85 (6H, d, J=6.2 Hz), 0.96 (3H, d, J=6.6 Hz), 1.4 (7H, m), 2.10 (1H, m), 3.00 (2H, m), 6.02 (2H, s). MS (FAB) m/z 281 (M+1)+.

Example 2
Synthesis of (2-methylpropyl) (2,4,5-trihydroxyphenyl) ketone (7)

In a vessel fitted with a calcium chloride tube, 12.61 g (100.0 mmol) of hydroxyhydroquinone (2) was suspended in 110 ml of nitrobenzene and stirred at room temperature. Into this, 40.0 g (300 mmol, 3.00 equivalents) of granular aluminum chloride was added piecemeal. They were further stirred for one hour and then 12.06 g (100.0 mmol, 1.00 equivalent) of isovaleryl chloride was slowly added dropwise. As the reaction mixture became a reddish purple amorphous solid 10 hours after the addition, it was mechanically crushed into fine fragments. The fine fragments were poured into 500 ml of a cold 2 M hydrochloric acid solution, stirred for 30 minutes, and extracted from ether. The ether layer was washed with water, distilled to remove the solvent, combined with a large volume of water, and distilled water under reduced pressure to remove nitrobenzene by steam distillation method. The residue of the distillation was dissolved in ether, washed with saturated brine, dried over sodium sulfate, distilled under a reduced pressure to remove ether and obtain a crude reaction product. By recrystallizing the crude product from hexane-petroleum ether (2:1), 18.3 g (yield 86.6%) of the product (7) was obtained in the form of reddish purple crystals of thin needles.

1HNMR δ (TMS): 0.96 (6H, d, J=6.6 Hz), 2.18 (1H, sept, J=6.6 Hz), 2.69 (2H, d, J=6.9 Hz), 6.50 (1H, s), 7.17 (1H, s), 8.6 (2H, bs), 10.1 (1H, bs).

Referential Example 3
Synthesis of (2-propyl) (2,3,4,6-tetrahydroxyphenyl) ketone (8)

In a vessel fitted with a calcium chloride tube, 1.00 g (7.04 mmol) of 1,2,3,5-tetrahydroxybenzene (3) was dissolved in 20 ml of nitrobenzene and stirred. Into the stirred mixture, 2.82 g (21.1 mmol, 3.00 equivalents) of granular aluminum chloride was added piecemeal and stirred. One hour thereafter, a nitrobenzene (5.0 ml) solution of 0.750 g (7.04 mmol, 1.00 equivalent) of isobutyryl chloride was added dropwise. Ten hours thereafter, the reaction solution was poured into 100 ml of cold 2 M hydrochloric acid solution, stirred for 30 minutes, and then extracted from ether. The ether layer was washed with water, distilled to remove ether, combined with a large volume of water, and distilled water under reduced pressure to remove nitrobenzene by steam distillation. The residue was extracted from ether, washed with saturated brine, dried over sodium sulfate, and distilled under a reduced pressure to remove the solvent and obtain 1.38 g of crude product. By purifying the crude product by column chromatography (SiO₂, 20 g of Wako Gel C-300, hexane:ether=1:1), 441 mg (yield 65.9%) of the product (8) was obtained in the form of yellow powder crystals.

1HNMR δ (TMS): 1.10 (6H, d, J=6.7 Hz), 3.95 (1H, sept, J=6.7 Hz), 5.90 (1H, s), 8.62 (bs).

Referential Example 4
Synthesis of (2-methylpropyl) (2,3,4,6-tetrahydroxyphenyl) ketone (9)

Under an atmosphere of argon, 4.28 g (30.14 mmol) of 1,2,3,5-tetrahydroxybenzene (3) was dissolved by stirring in 70 ml of nitrobenzene. The solution was cooled with water. To the cold solution, 16.1 g (120.56 mmol, 4.00 equivalents) of granular aluminum chloride was added piecemeal and stirred. To the stirred mixture, 3.67 ml (30.1 mmol, 1.00 equivalent) of isovaleryl chloride was added dropwise. After 5 hours, the reaction solution was poured into 100 ml of a cold.2 M hydrochloric acid solution, stirred for 20 minutes, and extracted from ether. The organic layer was washed with water, distilled to remove ether, combined with a large volume of water, and distilled under reduced pressure to remove nitrobenzene. The residue was extracted from ether, washed with saturated brine, dried over sodium sulfate, and distilled under a reduced pressure to obtain a crude reaction product. By purifying the crude product by silica gel column chromatography (300 g of Wako Gel C-200, hexane:ethyl acetate=2:1), 1.85 g (yield 27.2%) of the product (9) was obtained in the form of yellow powder crystals.

1HNMR δ (TMS): 0.97 (6H, d, J=6.6 Hz), 2.25 (1H, m), 2.96 (2H, d, J=7.0 Hz), 6.02 (1H, s), 6.9 (1H, brs), 8.5 (1H, brs), 9.79 (1H, brs), 11.76 (1H, brs); LR-MS (E1, 70V, 300 μA) 226 (M$^+$), 211, 193, 169 (base), 69.

Referential Example 5

Synthesis of (2,3,4,6-tetrahydroxyphenyl) phenyl ketone (10)

Under a stream of argon, 1.30 g (9.15 mmol) of 1,2,3,5-tetrahydroxyphenol (3) was suspended in 13 ml of ether and 0.935 ml (9.15 mmol, 1.00 equivalent) of benzonitrile was added to the suspension with stirring. The resultant mixture was cooled with ice water and 0.624 g (4.57 mmol, 0.50 equivalent) of zinc chloride was added and they were stirred at room temperature for 6 hours by bubbling hydrogen chloride gas throughout. The aeration of the mixture with the gas was stopped and the mixture was left standing at 4° C. for 13 hours. From the tarry precipitates consequently formed was removed the ether layer by decantation. The precipitates were stirred in an ice bath and 39 ml of water was added and were then refluxed for 2 hours. The product of reflux was filtered while kept in hot and stand still to form red brown from the filtrate. By dissolving the crystals again in ether, filtering off insolubles from the solution, and concentrating, 0.97 g (yield 45.9%) of the product (10) was obtained in the form of orange powder crystals.

1H-NMR δ (TMS): 6.03 (1H, s), 7.33–7.66 (6H, m), 8.0–11.0 (3H, br); 13C-NMR δ (TMS): 95.3, 104.3, 125.0, 127.5, 128.2, 130.7, 141.8, 149.5, 153.8, 155.8, 198.9; LR-MS (E1, 70V, 300 μA) 246 (M$^+$, base), 168, 140, 105, 77, 69.

Referential Example 6
Synthesis of methyl (2,3,4,6-tetrahydroxyphenyl) ketone (11)

Under a stream of argon, 2.00 g (14.08 mmol) of 1,2,3,5-tetrahydroxyphenol (3) and 20 ml of ether were placed to form a suspension and 1.00 g (24.3 mmol, 1.73 equivalents) of acetonitrile was added to the suspension. While the resultant mixture was cooled with ice water, 0.70 g (5.14 mmol, 0.36 equivalent) of zinc chloride was added to the mixture and hydrogen chloride gas was bubbled at room temperature for four hours with stirring. The aeration of the mixture with the gas was stopped and the aerated mixture was left standing still at 4° C. for 13 hours. The ether layer was removed by decantation from the tarry precipitates consequently formed. The precipitates were stirred in an ice bath and 60 ml of water was added-to the stirred precipitates and they were heated under reflux for 4 hours. The product of the reflux, after adding a small amount of active carbon, was filtered while kept in hot. From the filtrate, yellow crystals were obtained as precipitates. By dissolving the crystals again in ether, removing the insoluble by filteration, and then concentrating the filtrate, 0.82 g (yield 31.8%) of the product (11) was obtained in the form of yellow platelike crystals.

1H-NMR (90 MHz, d$_6$-DMSO) δ (TMS): 2.61 (3H, s), 5.93 (1H, s), 7.0 (1H, brs), 9.5 (1H, brs), 11.76 (1H, s); LR-MS (E1, 70V, 300 μA) 184 (M$^+$), 169 (base), 69.

Example 3
Synthesis of {3,5-bis(3-methyl-2-butenyl)-2,4,6-trihydroxyphenyl} (2-propyl) ketone (12), 2,2-bis(3-methyl-2-butenyl)-3,5-dihydroxy-6-(2-methyl-1-oxopropyl) cyclohexa-3,5-dienone (13), and {3-(3-methyl-2-butenyl)-2,4,6-trihydroxyphenyl} (2-propyl) ketone (14)

Under an atmosphere of nitrogen, 600 mg (15.0 mmol, 3.00 equivalents) of an oily 60% sodium hydride was washed with dry hexane to remove paraffin. In this solution, 20 ml of dimethyl sulfoxide was placed and stirred at room temperature. To the resultant mixture, a dimethyl sulfoxide (5.0 ml) solution of 981 mg (5.00 mmol) of (2-propyl) (2,4,6-trihydroxyphenyl) ketone (4) was added over a period of 15 minutes and stirred for 30 minutes. Then, a dimethyl sulfoxide (5.0 ml) solution of 1.43 g (10.0 mmol, 2.00 equivalents) of 1-bromo-3-methyl-2-butene was added dropwise over a period of 30 minutes. The resultant mixture was stirred at room temperature for 14 hours. The mixture was poured into 50 ml of a cold 2 M hydrochloric acid solution and extracted from ether. The ether layer was washed with saturated brine, dried over sodium sulfate, and distilled to remove the solvent and obtain 1.580 g of a crude product in the form of red oily substance. The crude product was separated by silica gel column chromatography (65 g of Wako Gel C-200, benzene:ethyl acetate=9:1) into (a) 239 mg of a brown viscous oily substance, (b) 342 mg of an orange color viscous oily substance, and (c) 206 mg of a yellow crystalline substance sequentially in the order of elution as indexed by the thin layer chromatography. The fraction (a) was further purified by column chromatography (15 g of Wako Gel C-300, petroleum ether:ether=9:1) to obtain 58 mg of {3,5-bis(3-methyl-2-butenyl)-2,4,6-trihydroxyphenyl} (2-propyl) ketone (12) in the form of yellow crystals.

1HNMR δ (TMS): 1.16 (6H, d, J=6.6 Hz), 1.78 (6H, s), 1.83 (6H, s), 3.38 (4H, bd), 3.99 (1H, sept, J=6.6 Hz), 5.22 (2H, m), 6.29 (1H, s), 10.14 (2H, s).

The fraction (b) was similarly purified by column chromatography (18 g of Wako Gel C-300, petroleum ether:ether=7:3) to obtain 197 mg of 2,2-bis(3-methyl-2-butenyl)-3,5-dihydroxy-6-(2-methyl-1-oxopropyl) cyclohexa-3,5-dienone (13) in the form of a yellow viscous substance.

1HNMR δ (TMS): 1.17 (6H, d, J=6.8 Hz), 1.58 (12H, bs), 2.62 (4H, bd), 3.98 (1H, sept, J=6.8 Hz), 4.85 (2H, m), 5.96 (1H, s).

The fraction (c) was treated by column chromatography (15 g of Wako Gel C-300, petroleum ether:ether=2:1) to obtain 110 mg of {3-(3-methyl-2-butenyl)-2,4,6-trihydroxyphenyl} (2-propyl) ketone (14) in the form of yellow crystals.

1HNMR δ (TMS): 1.13 (6H, d, J=6.6 Hz), 1.66 (3H, s), 1.76 (3H, s), 3.20 (2H, bd), 5.21 (1H, m), 6.02 (1H, s).

Example 4
Synthesis of {3,5-bis(3-methyl-2-butenyl)-2,4,6-trihydroxyphenyl} (2-propyl) ketone (12) and 2,2-bis(3-methyl-2-butenyl)-3,5-dihydroxy-6-(2-methyl-1-oxopropyl)-cyclohexa-3,5-dienone (13)

Under an atmosphere of nitrogen, 981 mg (5.00 mmol) of (2,4,6-trihydroxyphenyl) (2-propyl) ketone (4) was dissolved in 10.0 ml of dioxane, cooled with cold water at about 10° C., and stirred. Into the stirred solution, 554 ml (639 mg, 4.50 mmol, 0.900 equivalent) of boron trifluorideether complex was added by the use of a microsyringe. The resultant mixture was further stirred for 15 minutes and then a dioxane (9 ml) solution of 861 mg of 3-methyl-2-butenol was slowly added dropwise. After four hours, the reaction solution was poured into 100 ml of ether. The ether layer was washed sequentially with a saturated aqueous sodium hydrogen carbonate solution and saturated brine and dried over sodium sulfate. The produced solution was distilled under a reduced pressure to remove the solvent and obtain 1.76 g of a crude product in the form of a red viscous oily substance. The crude product was treated by silica gel column chromatography (50 g of Wako Gel C-300, and eluted sequentially with 200 ml each of petroleum ether:ether at varying ratios=9:1, 7:3, and 5:5) to isolate 417 mg of {3-(3-methyl-2-butenyl)-2,4,6-trihydroxyphenyl} (2-propyl) ketone (23) and 338 mg of 2,2-bis(3-methyl-2-butenyl)-3,5-dihydroxy-6-(2-methyl-1-oxopropyl) cyclohexa-3,5-dienone (13).

Example 5

Synthesis of {3,5-bis(3-methyl-2-butenyl)-2,4,6-trihydroxyphenyl} (2-methylpropyl) ketone (15), 3,5-dihydroxy-6-(3-methyl-1-oxobutyl)-2,2,4-tris(3-methyl-2-butenyl)cyclohexa-3,5-dienone (16), and 2,2-bis(3-methyl-2-butenyl)-3,5-dihydroxy-6-(3-methyl-1-oxobutyl)cyclohexa-3,5-dianone (17)

Under an atmosphere of nitrogen, 441 mg (11.1 mmol, 2.06 equivalents) of an oily 60% sodium hydride was washed with dry hexane to remove paraffin. To this was added 6.0 ml of dry methanol cooling with ice and stirred. Then, a methanol (6.0 ml) solution of 1.135 g (5.400 mmol) of (2-methylpropyl) (2,4,6-trihydroxyphenyl) ketone (5) was added dropwise to the solution. Further, a methanol (5.0 ml) solution of 1.205 g (11.52 mmol, 2.130 equivalents) of 1-chloro-3-methyl-2-butene was slowly added dropwise. The mixture was stirred cooling with ice for 1.5 hours, then added 50 ml of a saturated aqueous ammonium chloride solution, and extracted from ether. The ether layer was washed with saturated brine, dried over sodium sulfate, and distilled under a reduced pressure to remove the solvent and obtain 1.752 g of a crude product in the form of a red viscous oily substance. This crude product was subjected to silica gel column chromatography (40 g of Wako Gel C-300 and eluted sequentially with 200 ml each of petroleum ether:ether at varying ratios=19:1, 18:2, 17:3, and 16:4). From the eluate of the column, various fractions were sequentially obtained. As the first fraction, 160 mg of {3,5-bis(3-methyl-2-butenyl)-2,4,6-trihydroxyphenyl} (2-methylpropyl) ketone (15) was obtained in the form of light yellow crystals shaped fine needles.

1HNMR δ (TMS): 0.96 (6H, d. J=6.6 Hz), 1.78 (6H, s), 1.83 (6H, s), 2.26 (1H, sept, J=6.6 Hz), 2.94 (2H, d, J=6.6 Hz), 3.37 (4H, d, J=6.2 Hz), 5.22 (2H, m), 6.26 (1H, bs), 10.12 (2H, bs).

As the second fraction, 549 mg of 3,5-dihydroxy-6-(3-methyl-1-oxobutyl)-2,2,4-tris(3-methyl-2-butenyl)-cyclohexa-3,5-dienone (16) in the form of yellow crystals.

1HNMR δ (TMS): 0.96 (6H, d, J=6.6 Hz), 1.56 (15H, s), 1.78 (3H, s), 2.11 (1H, sept, J=6.6 Hz), 2.60 (4H, m), 2.92 (2H, d, J=6.9 Hz), 3.19 (2H, d, J=7.3 Hz), 4.79 (2H, m), 5.11 (1H, m).

As the third fraction, 259 mg of 2,2-bis(3-methyl-2-butenyl)-3,5-dihydroxy-6-(3-methyl-1-oxobutyl)cyclohexa-3,5-dienone (17) was obtained in the form of a yellow viscous oily substance.

1HNMR δ (TMS): 0.99 (6H, d, J=6.6 Hz), 1.57 (12H, bs), 2.16 (1H, sept, J=6.6 Hz), 2,62 (4H, m), 2.95 (2H, d, J=6.9 Hz), 4.84 (2H, m), 5.65 (1H, s).

Example 6

Synthesis of {3,5-bis(3-methyl-2-butenyl)-2,4,6-trihydroxyphenyl} (2-methylpropyl) ketone (15), 3,5-dihydroxy-6-(3-methyl-1-oxobutyl)-2,2,4-tris(3-methyl-2-butenyl)cyclohexa-3,5-dienone (16), and 2,2-bis(3-methyl-2-butenyl)-3,5-dihydroxy-6-(3-methyl-1-oxobutylcyclohexa-3,5-dienone (17)

Under an atmosphere of nitrogen, 2.244 g (20.00 mmol, 2.000 equivalents) of potassium t-butoxide was dissolved in 20.0 ml of dry methanol and the resultant solution was stirred cooling with ice. To the solution, a methanol (10.0 ml) solution of 2.102 g (10.00 mmol) of (2-methylpropyl) (2,4,6-trihydroxyphenyl) ketone (5) was added dropwise and then a methanol (15.0 ml) solution of 2.861 g (20.00 mmol, 2.000 equivalents) of 1-bromo-3-methyl-2-butene was further added slowly. The mixture was stirred cooling with ice for one hour and then at room temperature for two hours and then extracted by ether. The organic layer was washed with saturated brine, dried over sodium sulfate, and distilled under a reduced pressure to remove the solvent and obtain 2.932 g of a crude product in the form of a red viscous oily substance. The crude product was subjected to silica gel column chromatography (100 g of Wako Gel C-300 and eluted sequentially with 400 ml each of petroleum ether:ether at varying ratios=9:1, 8:2, 7:3, and 6:4). Consequently, the isolation of 117 mg of {3,5-bis(3-methyl-2-butenyl)-2,4,6-trihydroxyphenyl} (2-methylpropyl) ketone (15), 153 mg of 3,5-dihydroxy-6-(3-methyl-1-oxobutyl)-2,2,4-tris(3-methyl-2-butenyl)-cyclohexa-3,5-dienone (16), and 235 mg of 2,2-bis(3-methyl-2-butenyl)-3,5-dihydroxy-6-(3-methyl-1-oxobutyl)cyclohexa-3,5-dienone (17) was confirmed, with a thin layer chromatography as an index.

Example 7

Synthesis of 2,2-bis(3-methyl-2-butenyl)-3,5-dihydroxy-6-(3-methyl-1-oxobutyl)cyclohexa-3,5-dienone (17) and {3-(3-methyl-2-butenyl)-2,4,6-trihydroxyphenyl} (2-methylpropyl) ketone (18)

Under an atmosphere of nitrogen, 1.47 g (7.00 mmol) of (2-methylpropyl) (2,4,6-trihydroxyphenyl) ketone (5) was dissolved in 14.0 ml of dry dioxane and the solution was stirred in cold water (10° C.). To the solution, 690 ml (795 mg, 5.60 mmol, 0.80 equivalent) of boron trifluoride ether complex was added by the use of a microsyringe and then a dioxane (10.0 ml) solution of 1.21 g (14.0 mmol, 2.00 equivalents) of 3-methyl-2-butenol was added dropwise over a period of about 0.5 hour. The resultant mixture was stirred at room temperature for 14 hours and then was added 140 ml of ether. The organic layer was washed sequentially with a saturated aqueous sodium hydrogen carbonate solution and then with saturated brine, dried over sodium sulfate, and distilled under a reduced pressure to remove the solvent and obtain 2.93 g of a crude product in the form of a red viscous oily substance. The crude product was subjected to silica gel column chromatography (100 g of Wako Gel C-300 and eluted sequentially with 200 ml each of petroleum ether:ether at varying ratios=9:1, 8:2, 7:3, 6:4, and 5:5). With a thin layer chromatography as an index, as the first fraction, 427 mg of an oily substance was gathered and subjected again to silica gel column chromatography (17 g of Wako Gel C-300, eluted with petroleum ether ether=8:2) to isolate 311 mg of 2,2-bis(3-methyl-2-butenyl)-3,5-dihydroxy-6-(3-methyl-1-oxobutyl)cyclohexa-3,5-dienone (17).

The subsequent fraction of eluate, i.e. 613 mg of an oily substance, was subjected again to silica gel column chromatography (21 g of Wako Gel C-300, and eluted with petroleum ether:ether=7:3) to obtain 459 mg of {3-(3-methyl-2-butenyl)-2,4,6-trihydroxyphenyl} (2-methylpropyl) ketone (18) in the form of light yellow crystals.

1HNMR δ (TMS): 0.96 (6H, d, J=6.6 Hz), 1.71 (3H, s), 1.77 (3H, s), 2.23 (1H, sept, J=6.6 Hz), 2.95 (2H, d, J=6.3 Hz), 3.31 (2H, bd), 5.22 (1H, m), 5.95 (1H, m). cl Example 8

Synthesis of {3,5-bis(3,7-dimethyl-2,6-octadienyl)-2,4,6-trihydroxyphenyl} (2-methylpropyl) ketone (19), 3,5-dihydroxy-6-(3-methyl-1-oxobutyl)-2,2,4-tris(3,7-dimethyl-2,6-octadienyl)cyclohexa-3,5-dienone (20), and 2,2-bis(3,7-dimethyl-2,6-octadienyl)-3,5-dihydroxy-6-(2-methyl-1-oxobutyl)cychlohexa-3,5-dienone (21)

Under an atmosphere of nitrogen, 400 mg (10.0 mmol, 2.00 equivalents) of an oily paraffin dispersion of 60% sodium hydride was washed with hexane. A sodium methoxide solution was prepared by adding 10.0 ml of dry methanol to the resultant solution cooling with ice. To this, was added a methanol (5.0 ml) solution of 1.051 g (5.000 mmol) of (2,4,6-trihydroxyphenyl) (2-methylpropyl) ketone (5) dropwise and then a methanol (8.0 ml) solution of 1.727 g (10.0 mmol, 2.000 equivalents) of 1-chloro-3,7-dimethyl-2,6-octadiene was added dropwise over a period of 0.5 hour. The mixture was then stirred at room temperature for one hour. The resultant mixture was combined with 40 ml of a saturated aqueous ammonium chloride solution and extracted by ether. The extract was washed with saturated brine, dried over sodium sulfate, and distilled under a reduced pressure to remove the solvent and obtain 2.527 g of a crude product in the form of a red viscous oily substance. The crude product was subjected to silica gel column chromatography (95 g of Wako Gel C-300, eluted with 300 ml each of hexane:ether at varying ratios=9:1, 8:2, 7:3, 6:4, and 5:5). The fractions of the eluate separated, analysed by thin layer chromatography as an index, and produced (a) 663 mg of an orange oily substance, (b) 196 mg of an orange viscous oily substance, and (c) 218 mg of an orange viscous oily substance.

The fraction (a) was further subjected to silica gel column chromatography (27 g of Wako Gel C-300, eluted with 150 ml each of hexane:ether at varying ratios=29:1, 28:2, and 27:3) to isolate 128 mg of (3,5-bis(3,7-dimethyl-2,6-octadienyl)-2,4,6-trihydroxy-phenyl} (2-methylpropyl) ketone (19). 1HNMR δ (TMS): 0.96 (6H, d, J=6.6 Hz), 1.60 (9H, s), 1.67 (9H, s), 2.07 (9H, m), 2.95 (2H, d, J=7.2 Hz), 3.39 (4H, d, J=9.0 Hz), 5.08 (2H, m), 5.34 (2H, m).

From the fraction (b), 3,5-dihydroxy-6-(3-methyl-1-oxobutyl)-2,2,4-tris(3,7-dimethyl-2,6-octadienyl)-cyclohexa-3,5-dianone (20) was obtained.

1HNMR δ (TMS): 0.98 (6H, d, J=6.6 Hz), 1.56 (12H, s), 1.64 (6H, s), 1.91 (12H, bs), 2.24 (1H, m), 2.65 (4H, m), 2.94 (2H, d, J=6.8 Hz), 3.45 (2H, d, J)=8.0 Hz), 4.95 (6H, m).

From the fraction (c), 2,2-bis(3,7-dimethyl-2,6-octadienyl)-3,5-dihydroxy-6-(2-methyl-1-oxobutyl)-cyclohexa-3,5-dienone (21) was obtained.

1HNMR δ (TMS): 0.97 (6H, d, J=6.6 Hz), 1.59 (bs) and 1.67 (b) (total 18H), 1.99 (9H, m), 2.58 (4H, m), 2.96 (2H, d, J=6.8 Hz), 4.99 (4H, m), 5.94 (1H, s).

Example 9

Synthesis of 3,5-dihydroxy-6-(3,7-dimethyl-1-oxooctyl)-2,2,4-tris(3-methyl-2-butenyl)cyclohexa-3,5-dienone (22) and {3-(3-methyl-2-butenyl)-2,4,6-trihydroxyphenyl} (2,6-dimethylheptyl) ketone (23)

To 0.432 g (6.16 mmol, 2.00 equivalents) of potassium methoxide, 1 ml of dry methanol was added cooling with ice. Then, they were stirred for 15 minutes. A methanol (4 ml) solution of 0.864 g (3.08 mmol) of (2,4,6-trihydroxyphenyl) (2,6-dimethylheptyl) ketone (6) was added dropwise to the solution and continued stirring cooling with ice for 30 minutes. To the mixture, 728 ml (6.47 mmol, 2.10 equivalents) of 1-chloro-3-methyl-2-butene was added dropwise, stirring at room temperature for 3.5 hours. The resultant mixture was combined with 20 ml of a saturated aqueous ammonium chloride solution, extracted by ether, washed with saturated brine, dried over sodium sulfate, and distilled under a reduced pressure to remove the solvent and obtain a crude product. By subjecting this crude product to silica gel column chromatography (50 g of Wako Gel C-300 and eluted with hexane:ether=7:3), 0.181 g of 3,5-dihydroxy-6-(3,7-dimethyl-1-oxooctyl)-2,2,4-tris(3-methyl-2-butenyl)cyclohexa-3,5-dienone (22) was obtained in the form of an oily substance.

1HNMR δ (TMS): 0.86 (6H, d, J=6.3 Hz), 0.94 (3H, d, J=6.6 Hz), 1.25 (7H, m), 1.57 (12H, s), 2.00 (1H, m), 2.67 (4H, d, J=6.9 Hz), 3.00 (2H, m), 4.84 (2H, 6, J=6.9 Hz). MS (EI) m/z 416 (M)$^+$.

Further, from the eluate with hexane:ether=6:4, 0.311 g of {3-(3-methyl-2-butenyl-2,4,6-trihydroxyphenyl} (2,6-dimethylheptyl) ketone (23) in the form of an oily substance.

1HNMR δ (TMS): 0.84 (6H, d, J=6.3 Hz), 0.92 (3H, d, J=7.3 Hz), 1.23 (7H, m), 1.76 (bs), 1.81 (bs), (total 6H), 2.10 (1H, m), 2.80 (2H, m), 3.13 (2H, m), 3.34 (2H, d, J=7.3 Hz), 5.24 (1H, m), 5.90 (1H, m). MS (EI) m/z 348 (M)$^+$.

Example 10

Synthesis of 2,2-bis(3-methyl-2-butenyl)-3,5-dihydroxy-6-(3,7-dimethyl-1-oxooctyl)cyclohexa-3,5-dienone (24)

To 0.619 g (8.82 mmol, 2 equivalents) of potassium methoxide, 5 ml of dry methanol was added cooling with ice and stirred for 15 minutes. To this, a methanol (5 ml) solution of 1.536 g (4.41 mmol) of 2,4,6-trihydroxyphenyl) (2,6-dimethylheptyl) ketone (6) was added dropwise and stirred cooling with ice for 30 minutes. Further, 1.093 ml (9.702 mmol, 2.20 equivalents) of 1-chloro-3-methyl-2-butene was added dropwise and stirred at room temperature for 4 hours. The mixture was combined with 80 ml of a saturated aqueous ammonium chloride solution, extracted by ether, washed with saturated brine, dried over sodium sulfate, and distilled under a reduced pressure to remove the solvent and obtain a crude product. By subjecting this crude product to silica gel column chromatography (80 g of Wako Gel C-300 and eluted with hexane:ether=99:1, 97:3, and 95:5), 0.305 g of 2,2-bis(3-methyl-2-butenyl)-3,5-dihydroxy-6-(3,7-dimethyl-1-oxooctyl)-cyclohexa-3,5-dienone (24) in the form of an oily substance.

1HNMR δ (TMS): 0.86 (6H, d, J=5.9 Hz), 0.93 (3H, d, J=6.2 Hz), 1.26 (7H, m), 1.57 (bs), 1.79 (bs) (total 18H), 2.00 (1H, m), 2.58 (4H, m), 2.97 (2H, m), 3.19 (2H, bd), 4.81 (2H, bt), 5.15 (1H, bt). MS (El) m/z 484 (M)$^+$.

Example 11

Synthesis of {3,6-bis(3-methyl-2-butenyl)-2,4,5-trihydroxyphenyl} (2-methylpropyl) ketone (25) and {3-(3-methyl-2-butenyl)-2,4,5-trihydroxyphenyl} (2-methylpropyl) ketone (26)

Under an atmosphere of nitrogen, a dioxane (20.0 ml) solution of 2.102 g (10.0 mmol) of (2,4,5-trihydroxyphenyl) (2-methylpropyl) ketone (7) was stirred cooling with ice. To the solution, 1230 ml (1.420 g, 10.00 mmol, 1.000 equivalent) of boron trifluoride ether complex was added and then a dioxane (16.0 ml) solution of 2.584 g (30.0 mmol) of 3-methyl-2-butenol was slowly added. The mixture was stirred cooling with ice for three hours and then left standing at room temperature for 14 hours. The mixture was combined with 200 ml of ether. The organic layer was washed with a saturated aqueous sodium hydrogen carbonate solution and saturated brine, dried over sodium sulfate, and distilled under a reduced pressure to remove the solvent and obtain 4.018 g of a crude product in the form of dark red oily substance. By subjecting this crude product to silica gel column chromatography (80 g of Wako Gel C-300 and eluted with 300 ml each of hexane:ether at varying ratios= 9:1, 8:2, 7:3, 6:4, and 5:5), 249 mg of {3,6-bis(3-methyl-2-butenyl)-2,4,5-trihydroxyphenyl} (2-methylpropyl) ketone (25) in the form of yellow crystals shaped fine needles.

1HNMR δ (TMS): 0.96 (6H, d, J=6.6 Hz), 1.74 (bs), 1.80 (bs) (total 12H), 2.25 (1H, sept, J=6.6 Hz), 2.72 (2H, d, J=7.0 Hz), 3.41 (2H, d, J=7.0 Hz), 3.48 (2H, d, J=7.0 Hz), 5.03 (1H, s), 5.03 (1H, m), 5.29 (1H, m), 6.30 (1H, s).

As a fraction of higher polarity, 231 mg of {3-(3-methyl-2-butenyl)-2,4,5-trihydroxyphenol} (2-methylpropyl) ketone (26) was isolated.

1HNMR δ (TMS): 0.98 (6H, d, J=6.5 Hz), 1.74 (3H, s), 1.82 (3H, s), 2.25 (1H, sept, J=6.5 Hz), 2.69 (2H, d, J=6.8 Hz), 3.43 (2H, d, J=7.0 Hz), 5.30 (1H, m), 7.12 (1H, s).

Example 12

Synthesis of {6-(3-methyl-2-butenyl)-2,4,5-trihydroxyphenyl} (2-methylpropyl) ketonemono(3-methyl-2-butenyl) ether (27) and (2,4,5-trihydroxyphenyl) (2-methylpropyl) ketonemono(3-methyl-2-butenyl) ether (28)

Under an atmosphere of nitrogen, 400 mg (10.0 mmol, 2.00 equivalents) of an oily 60% sodium hydride was washed with dry hexane to remove paraffin. A sodium methoxide solution was prepared by adding 10.0 ml of dry methanol to the dispersion cooling with ice. To this, a methanol (6.0 ml) solution of 1.051 g (5.000 mmol) of (2,4,5-trihydroxyphenyl) (2-methylpropyl) ketone (7) was added and then a methanol (8.0 ml) solution of 1.046 g (10.00 mmol, 2.000 equivalents) of 1-chloro-3-methyl-2-butene was slowly added. The resultant mixture was stirred at room temperature for two hours. This mixture was combined with 200 ml of ether, neutralized with 100 ml of a saturated aqueous ammonium chloride solution, washed with saturated brine, dried over sodium sulfate, and distilled under a reduced pressure to remove the solvent and obtain 1.730 g of a crude product in the form of a red viscous oily substance. This crude product, when subjected to the treatment of separation by silica gel column chromatography (50 g of Wako Gel C-300, eluted with 200 ml each of petroleum ether:ether at varying ratios=9:1, 8:2, 7:3, 6:4), afforded 68 mg of {6-(3-methyl-2-butenyl)-2,4,5-trihydroxyphenyl} (2-methylpropyl) ketonemono(3-methyl-2-butenyl) ether (27) in the form of yellow crystals shaped fine needles.

1HNMR δ (TMS): 0.87 (6H), d, J=6.4 Hz), 1.74 (s), 1.73 (s) (total 12H), 2.22 (1H, sept, J=6.4 Hz), 2.79 (2H, d, J=6.6 Hz), 3.56 (2H, d, J=5.6 Hz), 4.58 (2H, d, J=6.9 Hz), 5.17 (1H, m), 5.44 (1H, m), 5.44 (1H, s), 6.37 (1H, s).

From the fraction of higher polarity, 64 mg of (2,4,5-trihydroxyphenyl) (2-methylpropyl) ketone.mono(3-methyl-2-butenyl) ether (28) in the form of yellow crystals shaped needles.

1HNMR δ (TMS): 0.99 (6H, d, J=6.6 Hz), 1.74 (3H, s), 1.79 (3H, s), 2.75 (1H, m), 2.71 (2H,.d, J=6.6 Hz), 4.60 (2H, d, J=6.8 Hz), 5.46 (1H, m), 6.44 (1H, s), 7.22 (1H, s).

Example 13

Synthesis of 2,4-bis(3-methyl-2-butenyl)-6-(2-methyl-1-oxopropyl)-2,3,5-trihydroxycyclohexa-3,5-dienone (29)

Under an atmosphere of nitrogen, 125 mg (3.12 mmol, 3.00 equivalents) of an oily 60% sodium hydride was washed with hexane to remove the oily component and then the sodium hydride was suspended on 2.0 ml of dimethyl sulfoxide cooling with cold water. A dimethyl sulfoxide (1.5 ml) solution of 221 mg (1.04 mmol) of (1,2,3,5-tetrahydroxyphenyl) (2-propyl) ketone (8) was added dropwise to the suspension. After the mixture was stirred for 30 minutes, a dimethylsulfoxide (1.0 ml) solution of 327 mg (2.29 mmol, 2.20 equivalents) of 1-bromo-3-methyl-2-butene was slowly added dropwise to the mixture. The produced mixture was stirred at room temperature for one hour, then combined with 100 ml of ether, and neutralized with a saturated aqueous ammonium chloride solution. The ether layer was washed with saturated brine, dried over sodium sulfate, distilled under a reduced pressure to remove the solvent and obtained 318 mg of a crude produce in the form of an orange amorphous solid. The crude product was purified by silica gel column chromatography (10 g of Wako Gel C-300, eluted with hexane:ether=7:3) to isolate 90 mg of 2,4-bis(3-methyl-2-butenyl)-6-(2-methyl-1-oxopropyl)-2,3,5-trihydroxycyclohexa-3,5-dienone (29) in the form of a yellow viscous oily substance.

1HNMR δ (TMS): 1.13 (6H, d, J=6.9 Hz), 1.52 (s), 1.67 (s), 1.73 (s) (total 12 H), 2.51 (2H, d, J=7.2 Hz), 3.09 (2H, d, J=7.2 Hz), 3.71 (1H, sept, J=7.2 Hz), 5.00 (1H, m), 5.14 (1H, m).

Example 14

Synthesis of 2,4-bis(3-methyl-2-butenyl)-6-(1-oxoethyl)-2,3,5-trihydroxycyclohexa-3,5-dienone (30)

Under a stream of argon, 200 mg (4.89 mmol, 3.00 equivalents) of an oil dispersion of 60% sodium hydride was washed with hexane to remove the oil component. While the dispersion and 8.0 ml of dry dimethyl-sulfoxide added cooling with water were stirred, 300 mg (1.63 mmol) of 2-methylpropyl-(2,3,4,6-tetrahydroxyphenyl) ketone (9) was added and stirred for 40 minutes. To the mixture, was added 0.367 ml (3.26 mmol, 2.00 equivalents) of 1-chloro-3-methyl-2-butene dropwise and stirred for four hours. The produced mixture was combined with 4 ml of 2 M hydrochloric acid solution and extracted by ethyl acetate. The organic layer was washed with saturated brine, dried over sodium sulfate, concentrated under a reduced pressure, and subjected to silica gel chromatography (100 g of Wako Gel C-200, eluted with benzene:ethyl acetate:acetic acid= 8:1:0.1) to obtain 242.6 mg (yield 46.5%) of the product (30) in the form of yellow powdery crystals.

1H-NMR (90 MHz, CDCl$_3$) δ (TMS): 1.53–1.73 (12H, m), 2.51 (5H, m), 3.08 (2H, d, J=7.5), 5.07 (2H, m), 18.65 (1H, s); LR-MS (EI, 70V, 300 µA) 320 (M$^+$) 252, 196 (base), 69.

Example 15

Synthesis of 2,4-dimethyl-6-(3-methyl-1-oxobutyl)-2,3,5-trihydroxycyclohexa-3,5-dienone (31)

Under a stream of argon, 372 mg (9.30 mmol, 3.00 equivalents) of an oily dispersion of 60% sodium hydride was washed with hexane to remove the oily component. The suspension kept cooled with water and 7.0 ml of dry dimethyl sulfoxide added were stirred. To the suspension, 700 mg (3.10 mmol) of 2-methylpropyl-(2,3,4,6-tetrahydroxyphenyl) ketone (9) was added and stirred for 30 minutes. Further, 0.579 ml (9.30 mmol, equivalent) of methyl iodide was added dropwise to the mixture and stirred for four hours. The resultant mixture was combined with 3 ml of 2 M hydrochloric acid solution and 1 ml of an aqueous 10% sodium thiosulfate solution and extracted by ethyl acetate. The organic layer was washed with saturated brine, dried over sodium sulfate, concentrated under a reduced pressure, and subjected to silica gel chromatography (75 g of Wako Gel C-200, eluted with carbon tetrachloride:ethyl acetate:acetic acid=400:200:5) to obtain 224 mg (yield 28.4%) of the product (31) in the form of yellow powdery crystals.

1H-NMR (90 MHz, CDCl$_3$) δ (TMS): 0.97 (3H, d, J=6.6), 1.01 (3H, d, J=6.6), 1.58 (3H, s), 1.86 (3H, s), 2.15 (1H, m), 2.82 (2H, d, J=7.0), 4.45 (1H, brs), 7.42 (1H, brs), 18.92 (1H, s); 13C-NMR (90 MHz, CDCl$_3$) δ (TMS): 6.9, 22.5, 22.8, 26.7, 30.4, 46.8, 75.7, 104.9, 105.2, 168.9, 191.1, 196.4, 201.3; LR-MS (EI, 70V, 300 μA) 254 (M$^+$), 237, 211 (base), 180, 151, 57.

Example 16
Synthesis of 2,4-bis(3-methyl-2-butenyl)-6-benzoyl-2,3,5-trihydroxycyclohexa-3,5-dienone (32)

Under a stream of argon, 440 mg (11.0 mmol, 3.01 equivalents) of an oily dispersion of 60% sodium hydride was washed with hexane to remove the oil component. The dispersion kept cooled with cold water and 18.0 ml of dry dimethyl sulfoxide added were stirred together. To the stirred suspension, 900 mg (3.66 mmol) of phenyl-(2,3,4,6-tetrahydroxyphenyl) ketone (10) was added and stirred for 30 minutes. Further, 0.830 ml (7.32 mmol, 2.00 equivalents) of 1-chloro-3-methyl-2-butene was added dropwise stirring for two hours. The produced mixture was combined with 15 ml of a saturated aqueous ammonium chloride solution and 2 ml of 2 M hydrochloric acid solution and extracted by ether. The organic layer was washed with saturated brine, dried over sodium sulfate, concentrated under a reduced pressure, and subjected to silica gel chromatography (g of Wako Gel C-200, eluted with hexane ethyl acetate 4:1) to obtain 716 mg (yield 51.3%) of the product (32) in the form of yellow powdery crystals.

1H-NMR (90 HMz, CDCl$_3$) δ (TMS): 1.57–1.74 (12H, m), 2.63 (2H, d, J=7.5), 3.10 (2H, d, J=7.5), 4.5 (1H, brs), 5.14 (2H, m), 7.23–7.7 (6H, m), 18.65 (1H, s); 13C-NMR (90 MHz, CDCl$_3$) δ (TMS): 17.8, 18.1, 21.3, 25.7, 25.9, 42.0, 79.1, 105.2, 109.4, 116.1, 121.1, 127.9, 128.1, 131.5, 132.7, 136.9, 137.9, 168.8, 190.6, 193.5, 195, 2; LR-MS (EI, 70V, 300 μA) 382 (M$^+$), 314, 258, 229, 217, 180, 151, 105 (base), 77, 69.

Example 17
Synthesis of 2,4-bisbenzyl-6-(3-methyl-1-oxobutyl)-2,3,5-trihydroxycyclohexa-3,5-dienone (33)

Under a stream of argon, 212 mg (5.31 mmol, 2.40 equivalents) of an oily dispersion of 60% sodium hydride was washed with hexane to remove the oil component. While the dispersion kept cooled with cold water, 11.0 ml of dry dimethyl sulfoxide was added and stirred. To this, was added 500 mg (2.21 mmol) of 2-methylpropyl-(2,3,4,6-tetrahydroxyphenyl) ketone (9) and stirred for 40 minutes. To the produced mixture, 0.525 ml (4.42 mmol, 2.00 equivalents) of benzyl bromide was added dropwise and stirred for four hours. The resultant mixture was combined with 10 ml of a saturated aqueous ammonium chloride solution and extracted by ether. The organic layer was washed with saturated brine, dried over sodium sulfate, concentrated under a reduced pressure, and subjected to silica gel chromatography (100 g of Wako Gel C-200, eluted with hexane:ethyl acetate=3:2) to obtain 207 mg (yield 23.1%) of the product (33) in the form of yellow powdery crystals.

1H-NMR (90 MHz, CDCl$_3$) δ (TMS): 0.94 (6H, d, J=6.2), 2.25 (1H, m), 2–3 (2H, br), 2.66 (2H, m), 3.04 (2H, s), 3.62 (2H, s), 7.1–7.4 (10H, m), 18.3 (1H, brs); 13C-NMR (90 MHz, CDCl$_3$) δ (TMS): 22.7, 22.9, 25.7, 27.8, 47.2, 50.5, 60.6, 105.6, 107.6, 125.9, 127.5, 128.0, 128.3, 128.8, 130.4, 133.5, 140.7, 171.5, 189.2, 195.5, 200.3; LR-MS (E1, 70V, 300 μA) 406 (M$^+$), 322, 315 (base), 287, 259, 237, 209, 197, 181, 167, 91.

Example 18
Synthesis of {3,5-bisbenzyl-2,4,6-trihydroxyphenyl} (2-methylpropyl) ketone (34), 2,2-bisbenzyl-6-(2-methyl-1-oxobutyl)-3,5-dihydroxycyclohexa-3,5-dienone (35), and 2,2,4-trisbenzyl-6-(3-methyl-1-oxobutyl)-3,5-dihydroxycyclohexa-3,5-dienone (36)

Under a stream of argon, 738 mg (10.0 mmol, 2.00 equivalents) of potassium methoxide was dissolved in 25.0 ml of dry methanol cooling with ice and stirred. To this was added 1.05 g (5.00 mmol) of 2-methylpropyl-(2,4,6-trihydroxyphenyl) ketone (5) and stirred for one hour. Further, 1.19 ml (10.0 mmol, 2.00 equivalents) of benzyl bromide was added dropwise and stirred for four hours cooling with ice. The resultant mixture was combined with 10 ml of a saturated aqueous ammonium chloride solution, distilled under a reduced pressure to remove methanol, and extracted by ether. The organic layer was washed with saturated brine, dried over sodium sulfate, concentrated under a reduced pressure, and then subjected to silica gel chromatography (150 g of Wako Gel C-200, eluted with hexane:diethyl ether at varying ratios=19:1–9:1–4:1) to produce sequentially by fractionation in the order of elution 2,2-bisbenzyl-6-(2-methyl-1-oxobutyl)-3,5-dihydroxycyclohexa-3,5-dienone (35), 2,2,4-trisbenzyl-6-(3-methyl-1-oxobutyl)-3,5-dihydroxycyclohexa-3,5-dienone (36), and {3,5-bisbenzyl-2,4,6-trihydroxyphenyl} (2-methylpropyl) ketone (34) in the respective amounts of 54.9 mg (yield 2.8%), 507 mg (yield 21.1%), and 150 mg (yield 7.7%) invariably in the form of yellow powdery crystals. 2,2-Bisbenzyl-6-(3-methyl-1-oxobutyl)-3,5-dihydroxycyclohexa-3,5-dienone (35)

1H-NMR (90 MHz, CDCl$_3$) δ (TMS): 0.93 (6H, d, J=6.6), 2.23 (1H, m), 2.91 (2H, d, J=6.6), 3.99 (4H, s), 4.98, 5.53,5.98 (total 1H, s, brs, s), 6.90–7.47 (10H, m), 9.86, 10.4, 18.82 (total 2H, brs, brs, s); LR-MS (EI, 70V, 300 μA) 390 (M$^+$), 330 (base), 177, 91.

2,2,4-Trisbenzyl-6-(3-methyl-1-oxobutyl)-3,5-dihydroxycyclohexa-3,5-dienone (36)

1H-NMR (90 MHz, CDCl$_3$) δ (TMS): 0.78–1.04 (6H, m), 2.2 (1H, m), 2.73–3.58 (8H, m), 5.6, 6.2 (total 1H, each brs), 6.85–7.25 (15H, m), 18.68, 18.87 (total 1H, each s). LR-MS (EI, 70V, 300 μA) 480 (M$^+$), 389, 305, 91 (base).

3,5-Bisbenzyl-2,4,6-trihydroxyphenyl) (2-methylpropyl) ketone (34)

1H-NMR (90 MHz, CDCl$_3$) δ (TMS): 0.79–1.01 (6H, m), 1.5–2.4 (1H, m), 2.59–2.93 (4H, m), 3.43–3.27 (4H, m), 6.93–7.25 (10H, m), 18.2–18.93 (1H, m). LR-MS (E1, 70V, 30 μA) 390 (M$^+$), 299 (base), 91.

Example 19
Synthesis of {3,5-bis(3-methylbutyl)-2,4,6-trihydroxyphenyl} (2-methylpropyl) ketone (37)

In 22.0 ml of ethanol, 1.50 g (4.34 mmol) of {3,5-bis(3-methyl-2-butenyl)-2,4,6-trihydroxyphenyl} (2-methylpropyl) ketone (15) was dissolved. The solution was stirred with 924 mg (0.217 mmol, 5% equivalent) of 5% palladium carbon catalyst (water content up to 50%) under hydrogen atmosphere under ordinary pressure at room temperature for two hours. The solution was filtered and concentrated under a reduced pressure to form a brown oil. This oil was subjected to silica gel chromatography (using 100 g of Wako Gel C-200, eluted with hexane:ethyl acetate=10:1) to obtain 1.32 g (yield 86.6%) of the product (37) in the form of a colorless oily substance.

1H-NMR (400 MHz, CDCl$_3$) δ (TMS): 0.97 (18H, d, J=6.9), 1.37 (4H, m), 1.64 (2H, m), 2.27 (1H, m), 2.54 (4H, m), 2.96 (2H, d, J=6.8), 4.58 (1H, s), 5.31 (1H, s), 9.69 (1H, brs); 13C-NMR (400 MHz, CDCl$_3$) δ (TMS): 20.7, 22.5, 22.9, 25.2, 28.3, 38.2, 53.1, 105.1, 106.2, 157.5, 158.2, 206.1; LR-MS (EI, 70V, 300 μA) 350 (M$^+$), 293 (base), 279, 275.

Referential Example 7

Synthesis of (phenylmethyl) (2,4,6-trihydroxyphenyl) ketone (38)

In a solvent mixture of 45 ml of nitrobenzene and 45 ml of carbon disulfide, 12.61 g (100.0 mmol) of fluoroglucinol was added and stirred cooling with cold water. To this, 40.0 g (300 mmol, 3.00 equivalents) of aluminum chloride was added piecemeal with stirring, attached with a calcium chloride tube. To the resultant mixture, 15.46 g (100.0 mmol, 1.000 equivalent) of phenyl acetyl chloride slowly was added dropwise and stirred at room temperature for two hours. When the evolution of an acidic gas ceased, the solution was poured into dilute hydrochloric acid (prepared from 100 ml of concentrated hydrochloric acid and 400 ml of cold water) with stirring, and then extracted by ether. The ether layer was washed with saturated brine and removed ether under a reduced pressure. The residue was combined with water and distilled under a reduced pressure, subjected to steam distillation to remove nitrobenzene. The residue was again extracted by ether, washed with saturated brine, dried over sodium sulfate, and distilled to remove the solvent and obtain 26.02 g of a red viscous oily substance. The oily substance was combined with a small amount of methylene chloride and left standing until crystallization in a refrigerator to obtain 19.62 g of (phenylmethyl) (2,4,6-trihydroxyphenyl) ketone (38) in the form of light yellow powdery crystals.

(38) 1H-NMR (CDCl$_3$): 4.42 (2H, s), 5.93 (2H, s), 7.19–7.34 (5H, m).

Example 20

Synthesis of {3,5-bis(3-methyl-2-butenyl)-2,4,6-trihydroxyphenyl} (phenylmethyl) ketone (39), 3,5-dihydroxy-6-(phenylacetyl)-2,2,4-tris(3-methyl-2-butenyl)-cyclohexa-3,5-dienone (40), 3,5-dihydroxy-6-(phenylacetyl)-2,2-bis(3-methyl-2-butenyl)cyclohexa-3,5-dienone (41), and {3-(3-methyl-2-butenyl)-2,4,6-trihydroxyphenyl} (phenylmethyl) ketone (42)

Under an atmosphere of nitrogen, a dry methanol (3.0 ml) solution of 733 mg (3.00 mmol) of (phenylmethyl) (2,4,6-trihydroxyphenyl) ketone (38) was added cooling with ice and stirred to a dry methanol (6.0 ml) solution of 324 mg (6.00 mmol, 2.00 equivalents) of sodium methoxide. To the solution, a methanol (4.0 ml) solution of 627 mg (6.00 mmol, 2.00 equivalents) of 1-chloro-3-methyl-2-butene was slowly added. The resultant mixture was stirred for three hours. The mixture was distilled under a reduced pressure at room temperature to remove methanol and then combined with ether. The ether layer was washed with saturated brine, dried over sodium sulfate, and distilled to remove the solvent and obtain 1.027 g of a crude product. This crude product was subjected to silica gel column chromatography (46 g of Wako Gel C-300, eluted with hexane:ether at varying ratios=19:1–1:1) to produce sequentially by fractionation in the order of elution 13 mg of {3,5-bis(3-methyl-2-butenyl)-2,4,6-trihydroxyphenyl} (phenylmethyl) ketone (39) in the form of a yellow viscous oily substance, 98 mg of 3,5-dihydroxy-6-(phenylacetyl)-2,2,4-tris(3-methyl-2-butenyl)cyclohexa-3,5-dienone (40) in the form of a yellow viscous oily substance, 136 mg of 3,5-dihydroxy-6-(phenylacetyl)-2,2-bis(3-methyl-2-butenyl)cyclohexa-3,5-dienone (41) in the form of a yellow solid, and 165 mg of {3-(3-methyl-2-butenyl)-2,4,6-trihydroxyphenyl} (phenylmethyl) ketone (42) in the form of yellow crystals.

(39) 1H-NMR (CDCl$_3$): 1.79 (6H, d, J=1.2), 1.84 (6H, s), 3.37 (2H, d, J=7.3), 4.41 (2H, s), 5.22 (1H, m), 7.29 (5H, m); (40) 1H-NMR (CDCl$_3$): (major isomer) 1.54 (6H, s), 1.56 (6H, s), 1.77 (6H, s), 2.53 (2H, d, J=7.8), 2.64 (2H, d, J=7.3), 3.17 (2H, d, J=7.3), 4.74 (2H, m), 5.12 (1H, m), 7.29 (5H, m); (minor isomer) 1.54 (6H, s), 1.56 (6H, s), 1.77 (6H, s), 2.67 (2H, d, J=7.3), 3.21 (2H, d, J=7.3), 4.74 (2H, m), 5.12 (1H, m), 7.29 (5H, m); (41) 1H-NMR (CDCl$_3$): 1.52 (3H, s), 1.55 (3H, s), 1.56 (6H, s), 2.73 (4H, m), 4.41 (2H, s), 4.80 (1H, m); (42) 1H-NMR (CDCl$_3$): 1.68 (3H, s), 1.76 (3H, s), 3.26 (2H, d, J=7.0), 4.41 (2H, s), 6.00 (1H, s), 7.18–7.33 (5H, m).

Example 21

Synthesis of {3,5-bis(3,7-dimethyl-2,6-octadienyl)-2,4,6-trihydroxyphenyl} (phenylmethyl) ketone (43), 3,5-dihydroxy-6-(phenylacetyl)-2,2,4-tris(3,7-dimethyl-2,6-octadienyl)cyclohexa-3,5-dienone (44), 3,5-dihydroxy-6-(phenylacetyl)-2,2-bis(3,7-dimethyl-2,6-octadienyl) cyclohexa-3,5-dienone (45), and {3-(3,7-dimethyl-2,6-octadienyl)-2,4,6-trihydroxyphenyl} (phenylmethyl) ketone (46)

Under an atmosphere of nitrogen, a dry methanol (3.0 ml) solution of 733 mg (3.00 mmol) of (phenylmethyl) (2,4,6-trihydroxyphenyl) ketone (38) was added while stirred at room temperature to a dry methanol (6.0 ml) solution of 324 mg (6.00 nmol, 2.00 equivalents) of sodium methoxide. Further, a methanol (5.0 ml) solution of 1.036 g (6.00 mmol, 2.00 equivalents) of 1-chloro-3,7-dimethyl-2,6-octadiene was slowly added. They were stirred at room temperature for three hours and then at 60° C. for one hour. The produced mixture was distilled under a reduced pressure at room temperature to remove methanol and then combined with ether. The ether layer was washed with saturated brine, dried over sodium sulfate, and then distilled off the solvent and obtain 1.567 g of a crude product. This crude product was subjected to silica gel column chromatography (50 g of Wako Gel C-300, eluted with hexane:ether at varying ratios=19:1–6:1) to produce sequentially by fractionation in the order of elution 132 mg of {3,5-bis(3,7-dimethyl-2,6-octadienyl)-2,4,6-trihydroxyphenyl} (phenylmethyl) ketone (43) in the form of an orange viscous oily substance, 166 mg of 3,5-dihydroxy-6-(phenylacetyl)-2,2,4-tris(3,7-dimethyl-2,6-octadienyl)cyclohexa-3,5-dienone (44) in the form of a yellow viscous oily substance, 203 mg of 3,5-dihydroxy-6-(phenylacetyl)-2,2-bis(3,7-dimethyl-2,6-octadienyl) cyclohexa-3,5-dienone (45) in the form of an orange viscous oily substance, and 222 mg of {3-(3,7-dimethyl-2,6-octadienyl)-2,4,6-trihydroxyphenyl} (phenylmethyl) ketone (46) in the form of yellow crystals.

(43) 1H-NMR (CDCl$_3$): 1.59 (6H, s), 1.69 (12H, s), 1.97 (8H, m), 4.23 (2H, s), 5.05 (4H, m), 7.29 (5H, m); (44) 1H-NMR (CDCl$_3$): 1.54 (15H, s), 1.60 (3H, s), 1.64 (3H, s), 1.65 (3H, s), 1.69 (3H, s), 1.75–2.20 (4H, m), 3.20 (2H, d), 4.39 (2H, s), 4.79 (2H, m), 4.98 (2H, m), 5.04 (1H, m), 5.24 (1H, m), 7.29 (5H, m); (45) 1H-NMR (CDCl$_3$): 1.55 (9H, s), 1.65 (3H, s), 1.88 (8H, m), 2.63 (4H, m), 4.40 (2H, s), 4.85 (2H, m), 4.94 (2H, m), 7.28 (5H, m); (46) 1H-NMR (CDCl$_3$): 1.57 (3H, s), 1.65 (3H, s), 1.77 (3H, s), 2.00 (4H, m), 3.29 (2H, d, J=6.8), 4.41 (2H, s), 5.09 (1H, m), 5.24 (1H, m), 7.25 (5H, m).

Referential Example 8

Synthesis of (2,4-dihydroxy-6-methylphenyl) (2-methylpropyl) ketone (47)

Orcinol monohydride, 14.20 g (100.0 mmol), in 160 ml of benzene was heated to distill benzene. This step was carried out twice by way of an operation of dehydration. The product of dehydration was dissolved in 45 ml of nitrobenzene and 45 ml of carbon disulfide, and 26.7 g (200 mmol, 2.00 equivalents) of aluminum chloride was added piecemeal while cooled with cold water and stirred, with a calcium chloride tube attached. Then, 12.1 g (100 mmol, 1.00 equivalent) of isovaleryl chloride was slowly added dropwise and stirred at room temperature for 14 hours. After the stop of the evolution of an acidic gas was confirmed, the resultant reaction mixture was poured into dilute hydrochloric acid (prepared from 100 ml of concentrated hydrochloric acid and 400 ml of cold water), stirred, and then extracted by ether. The ether layer was washed with saturated brine and the ether was removed under a reduced pressure. The residue was combined with water added piecemeal and meanwhile distilled under a reduced pressure to remove nitrobenzene by steam distillation. The residue was extracted by ether, washed with saturated brine, dried over sodium sulfate, and distilled off the solvent and obtain 18.53 g of a crude product in the form of brown viscous oily substance. The crude product was subjected to silica gel column chromatography (220 g of Wako Gel C-200, eluted with hexane:ethyl acetate=9:1) to obtain 5.681 g of (2,4-dihydroxy-6-methylphenyl) (2-methylpropyl) ketone (47).

(47) 1H-NMR (CDCl$_3$): 0.97 (6H, d, J=6.5), 2.25 (3H, s), 2.27 (1H, m), 2.78 (2H, d, J=6.6), 6.23 (1H, s), 6.26 (1H, s).

Example 22

Synthesis of {2-hydroxy-6-methyl-4-(3-methyl-2-butenyloxy)phenyl} (2-methylpropyl) ketone (48), {2,4-dihydroxy-6-methyl-3-(3-methyl-2-butenyl)phenyl} (2-methylpropyl) ketone (49), and {4,6-dihydroxy-2-methyl-3-(3-methyl-2-butenyl)phenyl} (3-methylpropyl) ketone (50)

Under an atmosphere of nitrogen, 300 mg (7.50 mmol, 1.50 equivalents) of an oil dispersion of 60% sodium hydride was washed with petroleum ether to remove paraffin and then combined with 7.5 ml of dry methanol. Then, a methanol (5.0 ml) solution of 1.04 g (5.00 mmol) of (2,4-dihydroxy-6-methylphenyl) (2-methylpropyl) ketone (47) was added cooling with ice and stirred. Further, a methanol (5.0 ml) solution of 784 mg (7.50 mmol, 1.50 equivalents) of 1-chloro-3-methyl-2-butene was slowly added dropwise. The resultant mixture was stirred at room temperature for two hours. The mixture was combined with ether. The ether layer was washed with a saturated aqueous ammonium chloride solution and saturated brine, dried over sodium sulfate, and distilled to remove the solvent and obtain 1.296 g of a dark red oily substance. This oily substance was combined with a small amount of hexane and left standing in a refrigerator to recover 277 mg of the starting substance in the form of colorless needle crystals. The filtrate, 965 mg in weight, was subjected to silica gel column chromatography (49 g of Wako Gel C-300, eluted with hexane:ethyl acetate at varying ratios=29 1–7:3) to produce sequentially by fractionation in the order of elution 108 mg of {2-hydroxy-6-methyl-4-(3-methyl-2-butenyloxy)phenyl} (2-methylpropyl) ketone (48) in the form of a yellow oily substance, 78 mg of {2,4-dihydroxy-6-methyl-3-(3-methyl-2-butenyl) phenyl} (2-methylpropyl) ketone (49) in the form of colorless fine crystals, and 260 mg of a yellowish brown oily substance which was again purified by column chromatography (6.0 g of Wako Gel C-300, eluted with hexane:ethyl acetate=19:1) to obtain 162 mg of {4,6-dihydroxy-2-methyl-3-(3-methyl-2-butenyl)phenyl} (3-methylpropyl) ketone (50) in the form of a yellow viscous oily substance.

(48) 1H-NMR (CDCl$_3$): 0.97 (6H, d, J=6.6), 1.74 (3H, s), 1.79 (3H, s), 2.22 (1H, m), 2.55 (3H, s), 2.78 (2H, d, J=6.8), 4.51 (2H, d, J=6.8), 5.46 (1H, m), 6.30 (1H, s); (49) 1H-NMR (CDCl$_3$): 0.96 (6H, d, J=6.4), 1.74 (3H, s), 1.80 (3H, s), 2.28 (1H, m), 2.51 (3H, s), 2.77 (2H, d, J=6.6), 3.40 (2H, d, J=6.7), 5.27 (1H, m), 6.20 (1H, s); (50) 1H-NMR (CDCl$_3$): 0.92 (6H, d, J=6.6), 1.73 (3H, s), 1.79 (3H, s), 2.28 (1H, m), 2.41 (3H, s), 2.74 (2H, d, J=6.6), 3.31 (2H, d, J=6.6), 5.07 (1H, m), 6.26 (1H, s).

Example 23

Synthesis of {3,5-bis(3-methyl-2-butenyl)-2-hydroxy-6-methyl-4-(3-methyl-2-butenyloxy)phenyl} (2-methylpropyl) ketone (51), and {2,4-dihydroxy-6-methyl-3-(3-methyl-2-butenyl)phenyl} (2-methylpropyl) ketone (49)

To a solution of 1.04 g (5.00 mmol) of (2,4-dihydroxy-6-methylphenyl) (2-methylpropyl) ketone (47) in dry 1,4-dioxane (10.0 ml), under nitrogen atmosphere, added 710 mg (5.00 mmol, 1.00 equivalent) of boron trifluoride ether complex in dioxane (5.0 ml) at 10° C. with stirring. Then, added 861 mg (10.0 mmol, 2.00 equivalents) of 3-methyl-2-butenol in dioxane (5.0 ml) slowly, allowing to elevate to room temperature, and stirred for five hours. Added ether to the reaction mixture and washed the ether layer with saturated sodium hydrogen carbonate aqueous solution and saturated brine, and dried over sodium sulfate. By removal of the solvent, obtained orange-colored oily substance as a crude product. Column chromatographic separation on silica gel (65 g of Wako Gel C-300, eluted with hexane: ethyl acetate at varying ratios=19:1–7:3) gave, in the order of elution, 246 mg of {3,5-bis(3-methyl-2-butenyl)-2-hydroxy-6-methyl-4-(3-methyl-2-butenyloxy)phenyl}(2-methylpropyl) ketone (51) as a light yellow viscous oil and 95 mg of {2,4-dihydroxy-6-methyl-3-(3-methyl-2-butenyl) phenyl}(2-methylpropyl) ketone (49) as a light yellow fine needles.

(51) 1H-NMR (CDCl$_3$): 0.92 (6H, d, J=6.4), 1.74 (18H, m), 2.18 (1H, m), 2.38 (3H, s), 2.73 (2H, d, J=7.2), 3.31 (2H, d, J=8.4), 3.41 (2H, d, J=8.6), 3.94 (2H, d, J=6.8), 5.06 (2H, m), 5.37 (2H, m).

Referential Example 9

Synthesis of (2,4-dihydroxyphenyl)(2-methylpropyl) ketone (52)

Resorcinol, 5.506 g (50.00 mmol), was added to 45 ml of nitrobenzene and stirred cooling with cold water and 13.3 g (100 mmol, 2.00 equivalents) of aluminum chloride was added piecemeal and they were stirred, with a calcium chloride tube attached. Then, 6.03 g (50.0 mmol, 1.00 equivalent) of isovaleryl chloride was slowly added dropwise, stirred at room temperature for one hour, and further heated stirring at 90° C. for six hours. When the evolution of an acidic gas ceased, the resultant mixture was poured into dilute hydrochloric acid (prepared from 40 ml of concentrated hydrochloric acid and 160 ml of cold water) with stirring, and then extracted by ether. The ether layer was washed with saturated brine and removed by distillation under a reduced pressure. The residue, with water added piecemeal, was distilled under a reduced pressure and distilled off nitrobenzene by steam distillation method. The residue was extracted again by ether, washed with saturated brine, dried over sodium sulfate, and distilled to remove the solvent and obtain 8.952 g of a red viscous oily substance. This oily substance was purified by silica gel column chromatography (20 g of Wako Gel C-200, eluted with hexane:ether at varying ratios=8:2–7:3) to obtain 4.37 g of (2,4-dihydroxyphenyl) (2-methylpropyl) ketone (52) in the form of light yellow crystals.

Example 24

Synthesis of {2-hydroxy-4-(3-methyl-2-butenyloxy) phenyl} (2-methylpropyl) ketone (53) and (2,4-dihydroxy-3-(3-methyl-2-butenyl)phenyl) (2-methylpropyl) ketone (54)

Under an atmosphere of nitrogen, 486 mg (2.50 mmol) of (2,4-dihydroxyphenyl) (2-methylpropyl) ketone (52) and 784 mg (7.50 mmol, 3.00 equivalents) of 1-chloro-3-methyl-2-butene were dissolved in 7.0 ml of dry methanol. To the solution which was stirred at room temperature, a methanol (7.5 ml) solution of 405 mg (7.50 mmol, 3.00 equivalents) of sodium methoxide was slowly added dropwise. The resultant mixture was stirred at room temperature for three hours and then at 50° C. for one hour, and distilled at room temperature under a reduced pressure to remove methanol, and combined with ether. The ether layer was washed with a saturated aqueous ammonium chloride solution and saturated brine, dried over sodium sulfate, distilled off the solvent and obtain 661 mg of a red oily substance. The crude product was subjected to silica gel column chromatography (20 g of Wako Gel C-300, eluted with hexane:ether at varying ratios=50:1–4:1) to produce sequentially by fractionation in the order of elution 139 mg of {2-hydroxy-4-(3-methyl-2-butenyloxy)phenyl} (2-methylpropyl) ketone (53) in the form of a colorless oily substance and 41 mg of {2,4-dihydroxy-3-(3-methyl-2-butenyl)phenyl} (2-methylpropyl) ketone (54) in the form of colorless crystals.

(53) 1H-NMR (CDCl$_3$): 1.00 (6H, d, J=6.4), 1.75 (3H, s), 1.79 (3H, s), 2.26 (1H, m), 2.75 (2H, d, J=6.6), 4.53 (2H, d, J=6.8), 5.46 (1H, m), 6.42 (1H, d, J=2.4), 6.43 (1H, dd, J=9.6, 2.4), 7.64 (1H, d, J=9.6); (54) 1H-NMR (CDCl$_3$): 1.00 (6H, d, J=6.4), 1.76 (3H, s), 1.83 (3H, s), 2.26 (1H, m), 2.75 (2H, d, J=7.0), 3.44 (2H, d, J=7.0), 5.27 (1H, m), 6.36 (1H, d, J=8.8), 7.55 (1H, d, J=8.8).

Example 25

Synthesis of {2,4-dihydroxy-5-(3-methyl-2-butenyl) phenyl} (2-methylpropyl) ketone (55)

Under an atmosphere of nitrogen, 355 mg (2.50 mmol, 1.00 equivalent) of boron trifluoride ether complex was added at 10° C. to a dry 1,4-dioxane (5.0 ml) solution of 486 mg (2.50 mmol) of (2,4-dihydroxyphenyl) (2-methylpropyl) ketone (52). Then, a dioxane (2.0 ml) solution of 431 mg (5.00 mmol, 2.00 equivalents) of 3-methyl-2-butenol was slowly added dropwise and stirred at room temperature for 22 hours and then at 50° C. for three hours. The reaction mixture was combined with ether. The ether layer was washed with a saturated aqueous sodium hydrogen carbonate solution and saturated brine and dried over sodium sulfate.

The reaction mixture was distilled off the solvent and obtain 864 mg of a colorless oily substance. The crude product was subjected to silica gel column chromatography (25 g of Wako Gel C-300, eluted with hexane:ether at varying ratios=19:1–4:1) to obtain 136 mg of (2,4-dihydroxy-5-(3-methyl-2-butenyl) phenyl) (2-methylpropyl) ketone (55).

(55) 1H-NMR (CDCl$_3$): 1.01 (6H, d, J=6.6), 1.79 (6H, s), 2.26 (1H, m), 2.75 (2H, d, J=6.6), 3.30 (2H, d, J=8.3), 5.30 (1H, m), 6.36 (1H, s), 7.45 (1H, s).

Example 26

(1) Preparation of Cells

ICR mice 11–12 days old (purchased from Charles River Japan) were euthanized by anesthesia with ether and immediately immersed in 70% ethanol for disinfection. By the use of ophthalmologist scissors and pincers sterilized in advance with ethanol, femur and tibia were excised from the sacrificed mice and chopped into small pieces in an α-MEM culture medium (purchased from Flow Laboratories Corp.) containing 5% FBS (purchased from Irvine Scientific Corp.), 100 U/ml penicillin and 100 μg/ml streptomycin. The supernatant formed consequently was recovered by pipeting, cleaned with the culture broth, and suspended in a 5% FBS α-MEM culture broth to obtain bone cells containing osteoclast cells. The supernatant of a bone cell-floating liquid formed after 3 minutes' standing of the bone cells at rest was recovered and passed through a mesh (cell strainer, 70 μm, purchased from Falcon Corp.). The filtrate was adjusted to a cell concentration of $1\times10^7$/ml and used for the pit formation assay.

(2) Test by Pit Formation Assay

An ivory piece was cut into slices, 150 μm in thickness, by the use of a precision low-speed cutting machine (purchased from Buehler Corp.). Cylindrical holes, 6 mm in diameter, were perforated in the slices by the use of a one-hole punch. The ivory slices were immersed in 70% ethanol and subjected therein to an ultrasonic cleaning treatment twice each for five minutes and washed three times with a sterilized PBS and twice with the culture medium. The ivory slices were set in place on a 96-hole culture plate (purchased from Falcon Corp.). The perforated ivory slices on the culture plate, with a culture broth containing a given compound of the present invention prepared in a concentration of $2\times10^{-5}$ M added in a fixed volume of 100 μl (final medicine concentration $1\times10^{-5}$ M) to each of the holes and a culture broth containing prepared bone cells in a concentration of $1\times10^7$/ml placed in each of the holes, were cultured for three days in a 10% $CO_2$ incubator at 37° C. After the culture, the ivory slices were placed in an aqueous 2 N sodium hydroxide and the cells on the slices were removed by the use of a rubber spatula. The ivory slices were washed with water and methanol. The absorption pits formed in the ivory slices were dyed with Coomassie Brilliant Blue and were counted under a microscope. Though the numbers of absorption pits were naturally found to disperse among test lots, depending on the ratios of varying specie s of cells in the bone cell suspensions and the lots of animals used, satisfactorily uniform test results were found in one and the same test lot. The ratio of inhibition of osteolysis was calculated on the 100% scale, in which 0% stands for the number of absorption pits found in the culture broth in the presence of rPTH ($1\times10^{-8}$ M) and in the absence of a medicine and 100% for total absence of absorption pit.

The test described above was performed in a total of ten runs, Tests 1–10. The results are shown in Table 2 and Table 3. It is clearly noted from the results that the compounds of the present invention exhibited prominently high ratios of inhibition of osteolysis and, therefore, were useful as substances possessing an activity to repress osteolysis.

In the columns titled "Added medicine No." found in Table 2 and Table 3, the symbol (-) denotes a control involving no addition of medicine and the numerical No. denotes the No. of the compound mentioned above.

TABLE 2

| Compound No. added | | Concentration of compound (M) | No. of absorption pits (Mean ± SD) | Ratio of inhibition (%) |
|---|---|---|---|---|
| Test 1 | (-) | 0 | 80.1 ± 5.6 | 0 |
| | 13 | $10^{-5}$ M | 16.8 ± 3.6 | 79.0 |
| | 14 | $10^{-5}$ M | 26.0 ± 2.6 | 67.5 |
| | 15 | $10^{-5}$ M | 8.3 ± 2.4 | 89.6 |
| | 16 | $10^{-5}$ M | 0 | 100.0 |
| Test 2 | (-) | 0 | 201.8 ± 10.9 | 0 |
| | 25 | $0^{-5}$ M | 0 | 100.0 |
| | 26 | $10^{-5}$ M | 29.3 ± 4.8 | 85.5 |
| | 27 | $10^{-5}$ M | 38.8 ± 6.6 | 80.8 |

TABLE 2-continued

| Compound No. added | Concentration of compound (M) | No. of absorption pits (Mean ± SD) | Ratio of inhibition (%) |
|---|---|---|---|
| | 28 | $10^{-5}$ M | 61.3 ± 5.5 | 69.6 |
| | 33 | $10^{-5}$ M | 9.8 ± 1.8 | 95.1 |
| Test 3 | (−) | 0 | 98.9 ± 9.3 | 0 |
| | 29 | $10^{-5}$ M | 20.3 ± 2.1 | 79.5 |
| | 30 | $10^{-5}$ M | 21.4 ± 3.9 | 78.2 |
| | 32 | $10^{-5}$ M | 33.9 ± 4.1 | 65.7 |
| Test 4 | (−) | 0 | 162.6 ± 17.8 | 0 |
| | 24 | $10^{-5}$ M | 39.3 ± 13.9 | 75.8 |
| | 37 | $10^{-5}$ M | 14.4 ± 4.9 | 91.1 |
| Test 5 | (−) | 0 | 187.7 ± 21.0 | 0 |
| | 6 | $10^{-5}$ M | 63.4 ± 12.4 | 61.4 |
| | 19 | $10^{-5}$ M | 55.3 ± 6.1 | 70.5 |
| | 20 | $10^{-5}$ M | 3.0 ± 1.3 | 98.4 |
| | 21 | $10^{-5}$ M | 3.5 ± 1.4 | 98.1 |
| | 22 | $10^{-5}$ M | 3.5 ± 1.1 | 98.1 |

TABLE 3

| Compound No. added | Concentration of compound (M) | No. of absorption pits (Mean ± SD) | Ratio of inhibition (%) |
|---|---|---|---|
| Test 6 | (−) | 0 | 201.8 ± 20.2 | 0 |
| | 34 | $10^{-5}$ M | 8.2 ± 1.9 | 95.9 |
| | 36 | $10^{-5}$ M | 3.8 ± 0.9 | 98.1 |
| | 47 | $10^{-5}$ M | 179.8 ± 23.8 | 10.9 |
| | 48 | $10^{-5}$ M | 85.2 ± 7.5 | 57.8 |
| | 49 | $10^{-5}$ M | 44.3 ± 5.4 | 78.0 |
| | 50 | $10^{-5}$ M | 40.1 ± 7.0 | 80.1 |
| | 51 | $10^{-5}$ M | 102.7 ± 6.2 | 42.8 |
| Test 7 | (−) | 0 | 179.6 ± 34.4 | 0 |
| | 39 | $10^{-5}$ M | 49.2 ± 9.4 | 72.6 |
| Test 8 | (−) | 0 | 125.3 ± 12.2 | 0 |
| | 38 | $10^{-5}$ M | 55.8 ± 7.7 | 57.9 |
| | 40 | $10^{-5}$ M | 4.9 ± 3.8 | 96.1 |
| | 41 | $10^{-5}$ M | 3.2 ± 0.7 | 97.4 |
| | 42 | $10^{-5}$ M | 31.7 ± 3.6 | 74.7 |
| Test 9 | (−) | 0 | 224.8 ± 20.0 | 0 |
| | 43 | $10^{-5}$ M | 11.3 ± 2.5 | 95.0 |
| | 44 | $10^{-5}$ M | 7.7 ± 2.0 | 96.6 |
| | 45 | $10^{-5}$ M | 8.2 ± 1.8 | 96.4 |
| | 46 | $10^{-5}$ M | 125.3 ± 12.6 | 44.3 |
| Test 10 | (−) | 0 | 171.2 ± 16.6 | 0 |
| | 52 | $10^{-5}$ M | 94.3 ± 13.8 | 44.9 |
| | 53 | $10^{-5}$ M | 55.1 ± 11.1 | 67.8 |
| | 54 | $10^{-5}$ M | 66.5 ± 9.7 | 61.2 |
| | 55 | $10^{-5}$ M | 15.8 ± 3.3 | 90.8 |

Translation of Annexes

Accompanying Internatinal Preliminary Examination Report

What we claim is:

1. A member of the group consisting of a compound of the formula

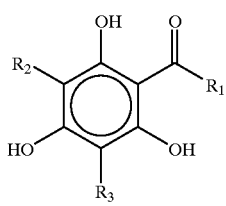

II wherein $R_1$ is 2-methylpropyl or 2,6-dimethylheptyl and $R_2$ and $R_3$ are individually selected from the group consisting of hydrogen, 3-methyl-2-butenyl, 3,7-dimethyl-2,6-octadienyl and benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid, providing that when $R_1$ is 2-methylpropyl, $R_2$ and $R_3$ are not hydrogen or 3-methyl-2-butenyl.

2. A compound of claim 1 wherein $R_2$ and $R_3$ are individually selected from the group consisting of hydrogen, 3-methyl-2-butenyl, 3,7-dimethyl-2,6-octadienyl and benzyl.

3. A member of the group consisting of a compound of the formula

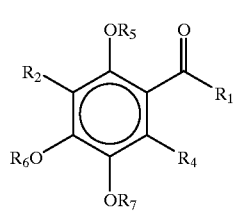

III wherein $R_1$ is selected from the group consisting of alkyl of 1 to 15 carbon atoms, benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid and optionally substituted aryl, $R_2$ and $R_4$ are individually selected from the group consisting of hydrogen, alkyl of 1 to 15 carbon atoms, alkenyl of 2 to 15 carbon atoms and optionally substituted benzyl, and $R_5$, $R_6$ and $R_7$ are individually selected from the group consisting of hydrogen, alkyl of 1 to 15 carbon atoms, alkenyl of 2 to 15 carbon atoms and benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid or a salt thereof with a non-toxic, pharmaceutically acceptable base.

4. A compound of claim 3 wherein $R_1$ is selected from the group consisting of 2-methylpropyl, 2,6-dimethylheptyl, benzyl, and phenyl or a salt thereof.

5. A compound selected from the group consisting of
{3,5-bisbenzyl-2,4,6-trihydroxyphenyl} (2-methylpropyl) ketone,
{3,5-bis(3,7-dimethyl-2,6-octadienyl)-2,4,6-trihydroxyphenyl} (2-methylpropyl) ketone,
{3-(3-methyl-2-butenyl)-2,4,5-trihydroxyphenyl} (2-methylpropyl) ketone,
{3,6-bis(3-methyl-2-butenyl)-2,4,5-trihydroxyphenyl} (2-methylpropyl) ketone,
{6-(3-methyl-2-butenyl)-2,4,5-trihydroxyphenyl} (2-methylpropyl) ketone mono(3-methyl-2-butenyl) ether,
(2,4,5-trihydroxyphenyl) (2-methylpropyl) ketone mono (3-methyl-2-butenyl) ether,
{3,5-bis(3-methyl-2-butenyl)-2,4,6-trihydroxyphenyl} (plenylmethyl) ketone,
{3-(3-methyl 2-butenyl)-2,4,6-trihydroxyphenyl} (phenylmethyl) ketone,
{3,5-bis(3,7-dimethyl-2,6-octadienyl)-2,4,6-trihydroxyphenyl} (phenylmethyl) ketone,
{3-(3,7-dimethyl-2,6-octadienyl)-2,4,6-trihydroxyphenyl} (phenylmethyl) ketone, {2-hydroxy-6-methyl-4-(3-methyl-2-butenyloxy)phenyl} (2-methylpropyl) ketone,
{2,4-dihydroxy-6-methyl-3-(3-methyl-2-butenyl)phenyl} (2-methylpropyl) ketone,
{4,6-dihydroxy-2-methyl-3-(3-methyl-2-butenyl)phenyl} (3-methylpropyl) ketone,
{3,5-bis(3-methyl-2-butenyl)-2-hydroxy-6-methyl-4-(3-methyl-2-butenyloxy)phenyl} (2-methylpropyl) ketone.
{2-hydroxy-4-(3-methyl-2-butenyloxy)phenyl} (2-methylpropyl) ketone,
{2,4-dihydroxy-3-(3-methyl-2-butenyl)phenyl} (2-methylpropyl) ketone, and
{2,4-dihydroxy-5-(3-methyl-2-butenyl)phenyl} (2-methylpropyl) ketone and a salt thereof.

6. A compound of the formula

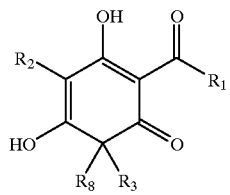

IV wherein $R_1$ is selected from the group consisting of alkyl of 1 to 15 carbon atoms, benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid, and aryl unsubstituted or substituted with at least one member of the group consisting of halogen, —OH, alkoxy of 1 to 15 carbon atoms, alkenyloxy of 2 to 15 carbon atoms and acyl of an organic carboxylic acid, $R_2$ is selected from the group consisting of hydrogen, alkyl of 1 to 15 carbon atoms, alkenyl of 2 to 15 carbon atoms, and optionally substituted benzyl, $R_3$ is selected from the group consisting of alkyl of 1 to 15 carbon atoms, alkenyl of 2 to 15 carbon atoms and benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid, and $R_8$ is selected from the group consisting of hydroxyl, alkyl of 1 to 15 carbon atoms, alkenyl of 2 to 15 carbon atoms, and benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid, with the proviso that when $R_2$ and $R_3$ are each 3-methyl-2-butenyl, $R_1$ is methyl and $R_8$ is hydroxyl and when two or three members of the class consisting of $R_2$, $R_3$, and $R_8$ are each 3-methyl-2-butenyl, the remaining member is not hydrogen or hydroxyl when $R_1$ is 2-propyl, 2-methylpropyl or 1-methylpropyl and a salt thereof with a non-toxic, pharmaceutically acceptable base.

7. A compound of claim 6 wherein $R_1$ is 2-methylpropyl, 2,6-dimethylheptyl, or phenyl and a salt thereof.

8. A compound of claim 6 wherein $R_2$ or $R_3$ are 3-methyl-2-butenyl, 3,7-dimethyl-2,6-octadienyl, or benzyl and a salt thereof.

9. A compound of claim 6 having the formula

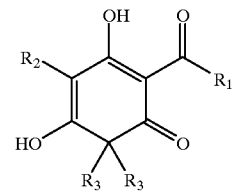

V wherein $R_1$ is 2-methylpropyl or 2,6-dimethylheptyl, $R_2$ is selected from the group consisting of hydrogen, 3-methyl-2-butenyl, 3,7-dimethyl-2,6-octadienyl and benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid, and $R_3$ is selected from the group consisting of 3-methyl-2-butenyl, 3,7-dimethyl-2,6-octadienyl and benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid, providing that when $R_1$ is 2-methylpropyl or 2-propyl, $R_2$ is hydrogen or 3-methyl-2-butenyl, $R_3$ is not 3-methyl-2-butenyl and a salt thereof.

10. A compound of claim 6 having the formula

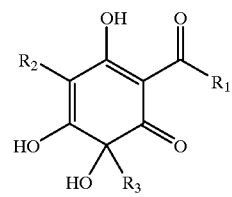

VI wherein $R_1$ is selected from the group consisting of 2-methylpropyl and aryl unsubstituted or substituted with at least one member of the group consisting of halogen, —OH, alkoxy of 1 to 15 carbon atoms, alkenyloxy of 2 to 15 carbon atoms and acyl of an organic carboxylic acid and $R_2$ and $R_3$ are individually 3-methyl-2-butenyl or benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid, providing that when $R_1$ is 2-methylpropyl, $R_2$ and $R_3$ are not each 3-methyl-2-butenyl and a salt thereof with a non-toxic, pharmaceutically acceptable base.

11. A compound of claim 6 selected from the group consisting of
2,2-bis(3,7-dimethyl-2,6-octadienyl)-3,5-dihydroxy-6-(3-methyl-1-oxobutyl)cyclohexa-3,5-dienone,
3,5-dihydroxy-6-(3-methyl-1-oxobutyl)-2,2,4-tris(3,7-dimethyl-2,6-octadienyl)cyclohexa-3,5-dienone,
2,2-bisbenzyl-3,5-dihydroxy-6-(3-methyl-1-oxobutyl)-cyclohexa-3,5-dienone,
3,5-dihydroxy-6-(3-methyl-1-oxobutyl)-2,2,4-trisbenzylcyclohexa-3,5-dienone,
2,2-bis(3-methyl-2-butenyl)-3,5-dihydroxy-6-(3,7-dimethyl-1-oxooctyl)cyclohexa-3,5-dienone,
3,5-dihydroxy-6-(3,7-dimethyl-1-oxooctyl)-2,2,4-tris(3-methyl-2-butenyl)cyclohexa-3,5-dienone,
2,4-bis(3-methyl-2-butenyl)-6-(benzoyl)-2,3,5-trihydroxycyclohexa-3,5-dienone, 2,4-dimethyl-6-(3-methyl-1-oxobutyl)-2,3,5-trihydroxycyclohexa-3,5-dienone, 2,4-bisbenzyl-6-(3-methyl-1-oxobutyl)-2,3,5-trihydroxycyclohexa-3,5-dienone, 3,5-dihydroxy-6-(phenylacetyl)-2,2,4-tris(3-methyl-2-butenyl)cyclohexa-3,5-dienone, 3,5-dihydroxy-6-(phenylacetyl)-2,2-bis(3-methyl-2-butenyl)cyclohexa-3,5-dienone, 3,5-dihydroxy-6-(phenylacetyl)-2,2,4-tris(3,7-dimethyl-2,6-octadienyl)cyclohexa-3,5-dienone, 3,5-dihydroxy-6-(phenylacetyl)-2,2-bis(3,7-dimethyl-2,6-octadienyl)cyclohexa-3,5-dienone or a salt thereof.

12. A composition for treating bones and cartilage comprising an effective amount of a compound of claim 1 and a pharmaceutically acceptable carrier.

13. A composition of claim 12 which is a curative agent for diseases affecting bones and cartilages.

14. A method for treating diseases of bones-cartilages in warm-blooded animals comprising administering to warm-blooded animals a compound of claim 1 in an amount effective in treating or preventing diseases of bones-cartilages.

15. A composition useful as a curative agent for diseases affecting bones-cartilages, comprising an effective amount of a compound of the formula

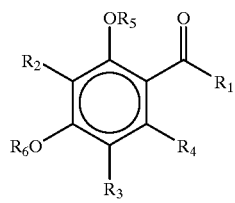

VII wherein $R_1$ is selected from the group consisting of alkyl of 1 to 15 carbon atoms, benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid and aryl unsubstituted or substituted with at least one member of the group consisting of halogen, —OH, alkoxy of 1 to 15 carbon atoms, alkenyloxy of 2 to 15 carbon atoms and acyl of an organic carboxylic acid, $R_2$ is selected from the group consisting of hydrogen, alkyl of 1 to 15 carbon atoms, alkenyl of 2 to 15 carbon atoms and benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid, $R_3$ is selected from the group consisting of hydrogen, alkyl of 1 to 15 carbon atoms, alkenyl of 2 to 15 carbon atoms, benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid, hydroxyl, alkoxy of 1 to 15 carbon atoms, alkenyloxy of 2 to 15 carbon atoms, benzyloxy unsubstituted or substituted with at least one member of the group consisting of halogen, —OH, alkoxy of 1 to 15 carbon atoms, alkenyloxy of 2 to 15 carbon atoms and acyl of an organic carboxylic acid, $R_4$ is selected from the group consisting of hydrogen, alkyl of 1 to 15 carbon atoms, alkenyl of 2 to 15 carbon atoms, benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid and hydroxyl, and $R_5$ and $R_6$ are individually selected from the group consisting of hydrogen, alkyl of 1 to 15 carbon atoms, alkenyl of 2 to 15 carbon atoms and benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid and a salt thereof with a non-toxic, pharmaceutically acceptable base and a pharmaceutically acceptable carrier.

16. A composition useful as a curative agent for diseases affecting bones-cartilages comprising a compound of the formula

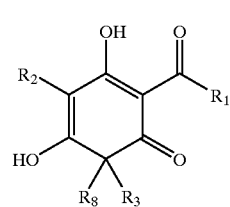

X wherein $R_1$ is selected from the group consisting of alkyl of 1 to 15 carbon atoms, benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid and aryl unsubstituted or substituted with at least one member of the group consisting of halogen, —OH, alkoxy of 1 to 15 carbon atoms, alkenyloxy of 2 to 15 carbon atoms and acyl of an organic carboxylic acid, $R_2$ is selected from the group consisting of hydrogen, alkyl of 1 to 15 carbon atoms, alkenyl of 2 to 15 carbon atoms and benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid, $R_3$ is selected from the group consisting of alkyl of 1 to 15 carbon atoms, alkenyl of 2 to 15 carbon atoms and benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid, and $R_8$ is selected from the group consisting of hydroxyl, alkyl of 1 to 15 carbon atoms, alkenyl of 2 to 15 carbon atoms and benzyl unsubstituted or substituted with at least one member of the group consisting of halogen, —OH, alkoxy of 1 to 15 carbon atoms, alkenyloxy of 2 to 15 carbon atoms and acyl of an organic carboxylic acid, providing that when $R_2$ and $R_3$ are each 3-methyl-2-butenyl, $R_1$ is methyl and $R_8$ is hydroxyl and in which two or three members of the class consisting of $R_2$, $R_3$, and $R_8$ are each 3-methyl-2-butenyl and the remaining member is hydrogen or hydroxyl when $R_1$ is not $R_2$-propyl, 2-methylpropyl or 1-methylpropyl and a salt of a non-toxic, pharmaceutically acceptable base and a pharmaceutically acceptable carrier.

17. A method for treating diseases of bones-cartilages in warm-blooded animals comprisi g administering to warm-blooded animals a compound of claim 1 in an amount effective to treat or prevent diseases of bones-cartilages.

* * * * *